United States Patent
Curtis et al.

(10) Patent No.: US 10,525,216 B2
(45) Date of Patent: *Jan. 7, 2020

(54) POWDER DISPERSION METHODS AND DEVICES

(71) Applicant: Respira Therapeutics, Inc., Albuquerque, NM (US)

(72) Inventors: Robert M. Curtis, Santa Fe, NM (US); Dan Deaton, Apex, NC (US); James Hannon, Albuquerque, NM (US); Hugh Smyth, West Lake Hills, TX (US); Zhen Xu, Albuquerque, NM (US); Martin Donovan, El Paso, TX (US); Aileen Gibbons, New York, NY (US)

(73) Assignee: Respira Therapeutics, Inc., Albuquerque, NM (US)

( * ) Notice: Subject to any disclaimer, the term of this patent is extended or adjusted under 35 U.S.C. 154(b) by 857 days.

This patent is subject to a terminal disclaimer.

(21) Appl. No.: 14/996,011

(22) Filed: Jan. 14, 2016

(65) Prior Publication Data

US 2016/0199598 A1 Jul. 14, 2016
US 2019/0224428 A9 Jul. 25, 2019

Related U.S. Application Data

(63) Continuation-in-part of application No. 13/773,325, filed on Feb. 21, 2013.
(Continued)

(51) Int. Cl.
*A61M 15/00* (2006.01)

(52) U.S. Cl.
CPC ...... *A61M 15/0086* (2013.01); *A61M 15/003* (2014.02); *A61M 15/0005* (2014.02);
(Continued)

(58) Field of Classification Search
CPC ............ A61M 15/0005; A61M 15/001; A61M 15/0085; A61M 15/0086
See application file for complete search history.

(56) References Cited

U.S. PATENT DOCUMENTS

| | | |
|---|---|---|
| 2,534,636 A | 12/1950 | Stirn |
| 2,579,280 A | 12/1951 | Trumbour et al. |
| (Continued) | | |

FOREIGN PATENT DOCUMENTS

| | | | |
|---|---|---|---|
| CN | 101856531 A | 10/2010 | |
| EP | 0147755 A2 * | 7/1985 | ........ A61M 15/0028 |
| (Continued) | | | |

OTHER PUBLICATIONS

International Search Report and Written Opinion dated Mar. 17, 2016, for International Application No. PCT/US2016/013456, 19 pages.
(Continued)

*Primary Examiner* — Joseph D. Boecker
(74) *Attorney, Agent, or Firm* — Kilpatrick Townsend & Stockton LLP

(57) ABSTRACT

A dry powder inhaler includes a powder storage element configured to hold a powdered medicament and an inlet channel receives powdered medicament from the powder storage element that is entrained in an airflow. The inlet channel has a first diameter and defines an opening. The inhaler includes a dispersion chamber that receives the airflow and the powdered medicament from the opening. The dispersion chamber has a second diameter. The inhaler includes an actuator housed within the dispersion chamber. The actuator oscillates within the dispersion chamber when exposed to the airflow to deaggregate the powdered medicament entrained by the airflow passing through the dispersion chamber. A ratio between the first diameter and the second diameter is between about 0.40 and 0.60 such that an
(Continued)

audible sound is produced as the actuator oscillates. The inhaler includes an outlet channel through which the airflow and powdered medicament exit the inhaler.

12 Claims, 31 Drawing Sheets

Related U.S. Application Data

(60) Provisional application No. 62/103,485, filed on Jan. 14, 2015, provisional application No. 61/601,400, filed on Feb. 21, 2012, provisional application No. 61/664,013, filed on Jun. 25, 2012.

(52) U.S. Cl.
CPC .... *A61M 15/0008* (2014.02); *A61M 15/0033* (2014.02); *A61M 15/0035* (2014.02); *A61M 15/0045* (2013.01); *A61M 15/0065* (2013.01); *A61M 2202/064* (2013.01); *A61M 2205/581* (2013.01)

(56) References Cited

U.S. PATENT DOCUMENTS

| | | | |
|---|---|---|---|
| 2,642,063 A | | 6/1953 | Brown |
| 3,837,341 A | | 9/1973 | Bell |
| 3,888,252 A | | 6/1975 | Side et al. |
| 3,888,253 A | * | 6/1975 | Watt .................. A61M 15/0028 128/203.15 |
| 3,888,262 A | | 6/1975 | Hollenton et al. |
| 3,971,377 A | | 7/1976 | Damani |
| 4,706,663 A | * | 11/1987 | Makiej .................. A61M 15/00 128/200.18 |
| 4,841,964 A | | 6/1989 | Hurka |
| 4,889,114 A | * | 12/1989 | Kladders ........... A61M 15/0028 128/203.15 |
| 4,995,385 A | | 2/1991 | Luigi et al. |
| 5,513,630 A | | 5/1996 | Century |
| 6,230,707 B1 | | 5/2001 | Horlin |
| 8,651,104 B2 | | 2/2014 | Donovan et al. |
| 9,492,625 B2 | | 11/2016 | Smyth et al. |
| 2002/0006316 A1 | | 1/2002 | Schuler et al. |
| 2003/0015195 A1 | | 1/2003 | Boer et al. |
| 2004/0069303 A1 | | 4/2004 | Brown |
| 2004/0089300 A1 | | 5/2004 | Miyamoto |
| 2004/0123865 A1 | | 7/2004 | Haikarainen et al. |
| 2005/0081850 A1 | | 4/2005 | Watt et al. |
| 2008/0035143 A1 | | 2/2008 | Sievers et al. |
| 2008/0115785 A1 | | 5/2008 | Eason |
| 2009/0084380 A1 | * | 4/2009 | Gieschen .......... A61M 15/0086 128/203.15 |
| 2009/0090362 A1 | | 4/2009 | Harmer et al. |
| 2010/0051023 A1 | * | 3/2010 | Kladders ........... A61M 15/0028 128/200.21 |
| 2011/0094507 A1 | | 4/2011 | Wachtel et al. |
| 2012/0145150 A1 | * | 6/2012 | Donovan ........... A61M 15/0028 128/203.15 |
| 2012/0291780 A1 | | 11/2012 | Donovan et al. |
| 2013/0042864 A1 | | 2/2013 | Adler et al. |
| 2013/0213397 A1 | * | 8/2013 | Curtis ................ A61M 15/0045 128/203.15 |
| 2013/0340747 A1 | * | 12/2013 | Donovan .......... A61M 15/0045 128/200.23 |
| 2013/0340754 A1 | * | 12/2013 | Donovan .......... A61M 15/0045 128/203.15 |
| 2015/0314086 A1 | * | 11/2015 | Curtis ................. A61M 15/009 128/203.15 |
| 2016/0199598 A1 | | 7/2016 | Curtis et al. |

FOREIGN PATENT DOCUMENTS

| | | |
|---|---|---|
| EP | 0388621 A1 | 9/1990 |
| WO | 2006037636 A1 | 4/2006 |
| WO | 2010040779 A2 | 4/2010 |
| WO | 2015001281 A1 | 1/2015 |

OTHER PUBLICATIONS

EP Patent Application No. 15751697.2 filed Feb. 20, 2015, Extended European Search Report dated Jan. 12, 2018, all pages.
EP Patent Application No. 15751697.2 filed Feb. 20, 2015, Communication pursuant to Rule 164(1) EPC dated Oct. 13, 2017, all pages.
U.S. Appl. No. 14/627,807, filed Feb. 20, 2015, Non-Final Office Action dated Dec. 13, 2017, all pages.
International Search Report and Written Opinion of PCT/US2015/016891 dated May 15, 2015, all pages.
International Preliminary Report on Patentability of PCT/US2015/016891 dated Sep. 1, 2016, all pages.
Final Office Action dated Jul. 6, 2018 in related U.S. Appl. No. 14/627,807, 6 pgs.
Non-Final Office Action dated Oct. 10, 2018 in related U.S. Appl. No. 14/627,807, 12 pgs.
Extended European Search Report dated Oct. 16, 2018, 27 pgs.
Supplementary Partial Search Report dated Jul. 9, 2018 in related foreign EU application No. EU16737900.7, 255 pgs.
Notice of Allowance dated Jun. 26, 2019 in related U.S. Appl. No. 13/773,325, 7 pgs.

\* cited by examiner

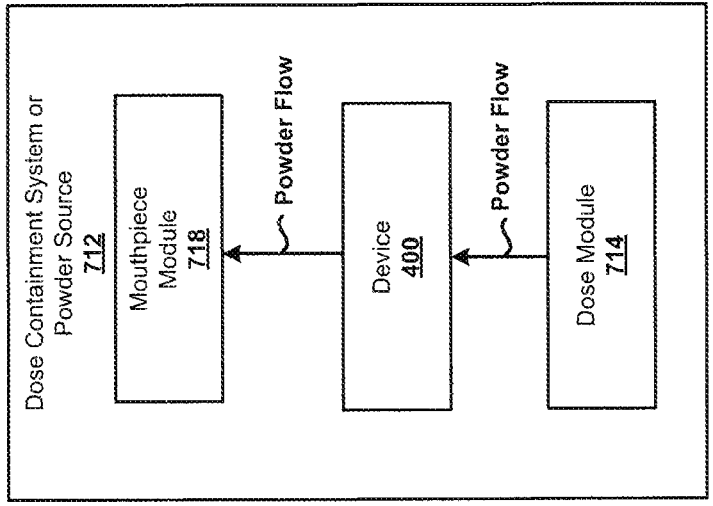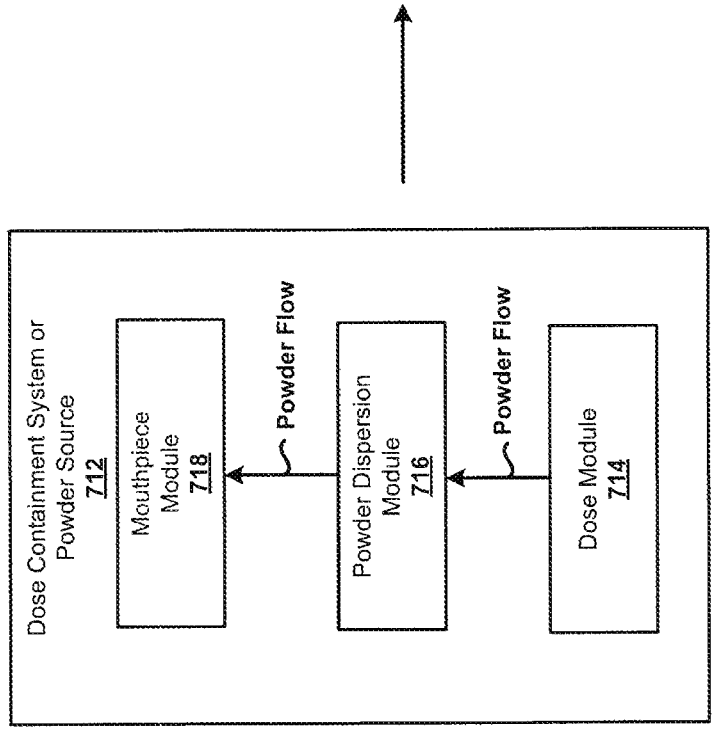
FIG. 8

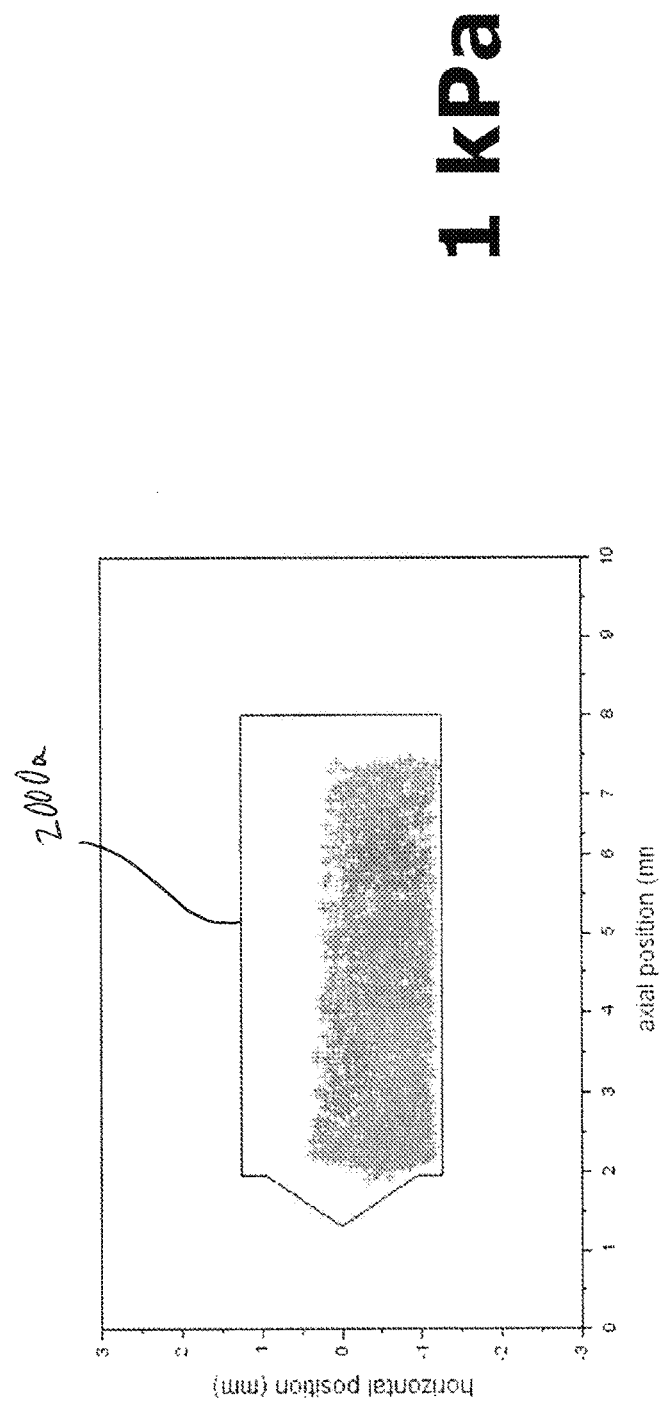

FIG.26

POWDER DISPERSION METHODS AND DEVICES

CROSS-REFERENCE TO RELATED APPLICATION

This application claims priority to U.S. Provisional Patent Application No. 62/103,485, filed on Jan. 14, 2015, entitled "POWDER DISPERSION METHODS AND DEVICES", this application also claims priority to and is a continuation-in-part of U.S. patent application Ser. No. 13/773,325, filed on Feb. 21, 2013, entitled "INHALER TO DELIVER SUBSTANCES FOR PROPHYLAXIS OR PREVENTION OF DISEASE OR INJURY CAUSED BY THE INHALATION OF BIOLOGICAL OR CHEMICAL AGENTS", which claims benefit to U.S. Provisional Patent Application No. 61/664,013, filed on Jun. 25, 2012, entitled "POWDER DISPERSION DEVICES AND METHODS" and U.S. Provisional Patent Application No. 61/601,400, filed on Feb. 21, 2012, entitled "INHALER TO DELIVER SUBSTANCES FOR PROPHYLAXIS OR PREVENTION OF DISEASE OR INJURY CAUSED BY THE INHALATION OF BIOLOGICAL OR CHEMICAL TERRORISM/WARFARE AGENTS", the entirety of which is hereby incorporated by reference for all purposes.

This application is related to U.S. Nonprovisional patent application Ser. No. 13/773,325, filed on 21 Feb. 2013, entitled "INHALER TO DELIVER SUBSTANCES FOR PROPHYLAXIS OR PREVENTION OF DISEASE OR INJURY CAUSED BY THE INHALATION OF BIOLOGICAL OR CHEMICAL AGENTS," the entirety of which is hereby incorporated by reference for all purposes.

This application is related to U.S. Nonprovisional patent application Ser. No. 13/776,546, filed on 25 Feb. 2013, entitled "POWDER DISPERSION DEVICES AND METHODS," the entirety of which is hereby incorporated by reference for all purposes.

This application is related to U.S. Nonprovisional patent application Ser. No. 13/776,558, filed on 25 Feb. 2013, entitled "POWDER DISPERSION DEVICES AND METHODS," the entirety of which is hereby incorporated by reference for all purposes.

BACKGROUND

In the field of dry powder inhalers, there is generally a trade-off between performance, as defined by the efficiency of the nominal or loaded dose in the inhaler that is delivered to the lung, and device complexity, in terms of the internal geometry, specifically, the powder flow path that the dose travels as it exits the device. In many instances, inhalers with relatively uncomplicated flow paths may be characterized by poor efficiency, as generally less than 30% of the nominal dose is delivered to the deep lung. Alternatively, inhalers with relatively more complex internal flow paths, may provide increased efficiency, such as less than or equal to 40% of the nominal dose, though the increased complexity of the internal flow path may lead to increased deposition within the inhaler, effectively lowering the overall dose delivered to the patient and contaminating the device. In addition, most dry powder inhalers available today have no means of providing feedback to the user that they have used the device correctly. Incorrect use may cause poor inhaler performance.

SUMMARY

This Summary does not in any way limit the scope of the claimed subject matter.

The present disclosure is directed to a powder dispersion mechanism that is compact, breath-actuated, provides audio feedback, and that is effective or sufficient at promoting efficient particle dispersion across a range of doses such as from, for example, low microgram doses to doses requiring many milligrams. Accordingly, in some embodiments, a powder dispersion mechanism is disclosed that employs an actuator contained within a dispersion chamber. An actuator is an element in the inhaler that may oscillate, generally linearly in certain embodiments, along an axis of the dispersion chamber when the patient inhales through the device, such that the actuator does not require an energy source other than a patient's inspiratory maneuver to function. This actuator may take various forms or shapes including a sphere, ball, or bead-like shape. However, the actuator is not limited to this and may take any appropriate shape that results in oscillation. In some embodiments, the powder dispersion mechanism may include a predominantly straight flow path, and may be breath-actuated. This may be referred to as "passive" actuator activation or actuation. During actuator oscillation the actuator may make an audible sound that could provide feedback for the user of the inhaler. However, the present disclosure is not so limiting. For example, actuator activation may be "active," where an external energy source is coupled with the patient's inhalation flow stream to induce actuator oscillation. One or more features of the inhaler may be such that a flow profile is generated within the dispersion chamber that prevents or at least minimizes unintended deposition or accumulation of powder within the chamber.

In an aspect, a dry powder inhaler is disclosed. The dry powder inhaler may include a first chamber that is adapted to receive an aerosolized powdered medicament from an inlet channel. A volume of the first chamber may be equal to, greater than or less than the volume of the inlet channel. The dry powder inhaler may include a dispersion chamber that is adapted to receive at least a portion of the aerosolized powdered medicament from the first chamber. The dispersion chamber may hold an actuator that is movable within the dispersion chamber along a longitudinal axis. The dry powder inhaler may include an outlet channel through which air and powdered medicament exit the inhaler to be delivered to a patient. A geometry of the inhaler may be such that a flow profile is generated within the dispersion chamber that causes the actuator to oscillate along the longitudinal axis, enabling the oscillating actuator to effectively disperse powdered medicament received in the dispersion chamber for delivery to the patient through the outlet channel. During actuator oscillation the actuator may generate an audible sound intended for feedback to the user.

In an aspect, a dry powder inhaler system is disclosed. The dry powder inhaler system may include a receptacle containing an amount of powdered medicament. The dry powder inhaler system may include an inlet channel that is adapted to receive air and powdered medicament from the receptacle. The dry powder inhaler system may include a first chamber that is adapted to receive air and powdered medicament from the inlet channel. A volume of the first chamber may be equal to, greater or less than the volume of the inlet channel. The dry powder inhaler system may include a dispersion chamber that is adapted to receive air and powdered medicament from the first chamber. The dispersion chamber may hold an actuator that is movable within the dispersion chamber along a longitudinal axis. The dry powder inhaler system may include an outlet channel through which air and powdered medicament exit the dispersion chamber to be delivered to a patient. A geometry of the system may be such that a flow profile is generated within the system that causes the actuator to oscillate along the longitudinal axis, enabling the oscillating actuator to effectively disperse powdered medicament received in the dispersion chamber for delivery to the patient through the outlet channel. During actuator oscillation the actuator may generate an audible sound intended for feedback to the user.

In an aspect, a method for aerosolizing a powdered medicament is disclosed. The method may include providing an inhaler comprising a first chamber, and a dispersion chamber, the dispersion chamber containing an actuator that is movable within the dispersion chamber along a longitudinal axis, and an outlet channel. The method may include inducing air flow through the outlet channel to cause air and powdered medicament to enter into the first chamber through the inlet channel into the dispersion chamber, and to cause the actuator to oscillate within the dispersion chamber to effectively disperse powdered medicament passing through the first chamber and the dispersion chamber to be entrained by the air and delivered to the patient through the outlet channel.

In another aspect a dry powder inhaler is provided. The inhaler may include a powder storage element configured to hold a powdered medicament and an inlet channel configured to receive powdered medicament from the powder storage element that is entrained in an airflow. The inlet channel may have a first diameter and may define an opening. The inhaler may also include a dispersion chamber that is adapted to receive the airflow and the powdered medicament from the opening of the inlet channel. The dispersion chamber may have a second diameter. The inhaler may further include an actuator housed within the dispersion chamber. The actuator may be configured to oscillate within the dispersion chamber when exposed to the airflow to deaggregate the powdered medicament passing through the dispersion chamber to be entrained by the airflow. A ratio between the first diameter and the second diameter may be between about 0.40 and 0.66 such that an audible sound is produced as the actuator oscillates. The inhaler may also include an outlet channel through which the airflow and powdered medicament exit the inhaler for delivery to a patient.

In another aspect, the dry powder inhaler may include a powder storage element configured to hold a powdered medicament and an inlet channel configured to receive powdered medicament from the powder storage element that is entrained in an airflow. The inlet channel may define an opening. The inhaler may include a dispersion chamber that is adapted to receive the airflow and the powdered medicament from the opening of the inlet channel. The dispersion chamber may have a length. The inhaler may further include a bead housed within the dispersion chamber. The bead may be configured to oscillate within the dispersion chamber when exposed to the airflow to deaggregate the powdered medicament passing through the dispersion chamber to be entrained by the airflow. The bead may have a diameter such that the length of the dispersion chamber is between about 2 and 3.5 times larger than the diameter of the bead such that an audible sound is produced as the bead oscillates. The inhaler may also include an outlet channel through which the airflow and powdered medicament exit the inhaler for delivery to a patient.

In another aspect, the dry powder inhaler may include a powder storage element configured to hold a powdered medicament and an inlet channel configured to receive powdered medicament from the powder storage element that is entrained in an airflow. The inlet channel may have a first diameter and may define an opening. The inhaler may also include a dispersion chamber that is adapted to receive the airflow and the powdered medicament from the opening of the inlet channel. The dispersion chamber may have a second diameter and a length. The inhaler may further include a bead housed within the dispersion chamber. The bead may be configured to oscillate within the dispersion chamber when exposed to the airflow to deaggregate the powdered medicament passing through the dispersion chamber to be entrained by the airflow. The bead may have a third diameter. A ratio between the first diameter and the second diameter may be between about 0.40 and 0.66 and the length may be between about 2 and 3.5 times larger than the third diameter such that an audible sound is produced as the bead oscillates. The inhaler may also include an outlet channel through which the airflow and powdered medicament exit the inhaler for delivery to a patient.

In another aspect, the dry powder inhaler may include a powder storage element configured to hold a powdered medicament and a conical frustum shaped inlet channel configured to receive powdered medicament from the powder storage element that is entrained in an airflow. The inhaler may also include a dispersion chamber that is adapted to receive the airflow and the powdered medicament from the opening of the inlet channel. The inhaler may further include an actuator housed within the dispersion chamber. The actuator may be configured to oscillate within the dispersion chamber when exposed to the airflow to deaggregate the powdered medicament passing through the dispersion chamber to be entrained by the airflow. The inhaler may also include an outlet channel through which the airflow and powdered medicament exit the inhaler for delivery to a patient.

In another aspect, the dry powder inhaler may include a powder storage element configured to hold a powdered medicament and an inlet channel configured to receive powdered medicament from the powder storage element that is entrained in an airflow. The inhaler may also include a dispersion chamber that is adapted to receive the airflow and the powdered medicament from the opening of the inlet channel. The airflow may be substantially coaxial with a longitudinal axis of the dispersion chamber. The inhaler may further include an actuator housed within the dispersion chamber. The actuator may be configured to oscillate within the dispersion chamber when exposed to the airflow to deaggregate the powdered medicament passing through the dispersion chamber to be entrained by the airflow. The inhaler may also include an outlet channel through which the airflow and powdered medicament exit the inhaler for delivery to a patient. Although not so limited, an appreciation of the various aspects of the present disclosure may be gained from the following discussion in connection with the drawings.

BRIEF DESCRIPTION OF THE DRAWINGS

FIG. 8 shows the device of FIG. 4 incorporated into an existing inhaler system.

FIGS. 20A-20C show bead position plots to determine chamber end contact for inlet diameters of 3.10 mm.

FIG. 26 shows the aerosol performance of a DPI of FIG. 24.

DETAILED DESCRIPTION

The present disclosure relates to the field of pulmonary drug or medicament delivery, and more specifically to dry powder inhalers that deliver a powder or medicament into the lungs of a patient. Such a powder dispersion mechanism may comprise of an actuator positioned within a chamber that is arranged and configured to induce a sudden, rapid, or otherwise abrupt expansion of a flow stream upon entering the chamber. During actuator oscillation the actuator may make an audible sound or response that could provide feedback to the user of the inhaler. Characteristics of the audible response may be adjusted based on various geometric properties of an inhaler, as well as material selection. Additionally, at least the chamber may be formed to exhibit one or more features that prevent or at least minimize the accumulation or build-up of powder in the chamber with the actuator. This may advantageously prevent the delivery of a macro dose of powder to a patient that may occur when an unintended deposit or residue of powder is broken-up or released during use. An actuator is an element in the inhaler that may oscillate, generally linearly in certain embodiments, along an axis of the dispersion chamber when the patient inhales through the device, such that the actuator does not require an energy source other than a patient's inspiratory maneuver to function. This actuator may take various forms or shapes including a sphere, ball, or bead-like shape. However, the actuator is not limited to this and may take any appropriate shape that results in oscillation.

Embodiments provide dry powder inhalers configured to produce an audible sound or feedback while delivering acceptable aerosol performance. The audible feedback is sufficiently loud that a user of the inhaler may be alerted when inhalations meet or exceed a minimum amount of flow. Suitable audio sound may be obtained by configuring a ratio ($d_{inlet}/d_{chamber}$) of an internal diameter of an inlet ($d_{inlet}$) of the inhaler to an internal diameter of a dispersion chamber of the inhaler ($d_{chamber}$) to be within a certain range, by configuring a ratio ($l_{chamber}/d_{bead}$) of a length of the dispersion chamber ($l_{chamber}$) relative to a diameter of the actuator or bead ($d_{bead}$) of the inhaler to be within a certain range or by certain combinations of both ($d_{inlet}/d_{chamber}$) and ($l_{chamber}/d_{bead}$). These ratios may be specifically selected so that they provide an acceptable audio sound while also ensuring proper aerosol performance (so that the powder can reach the deep lung).

Figure 1:
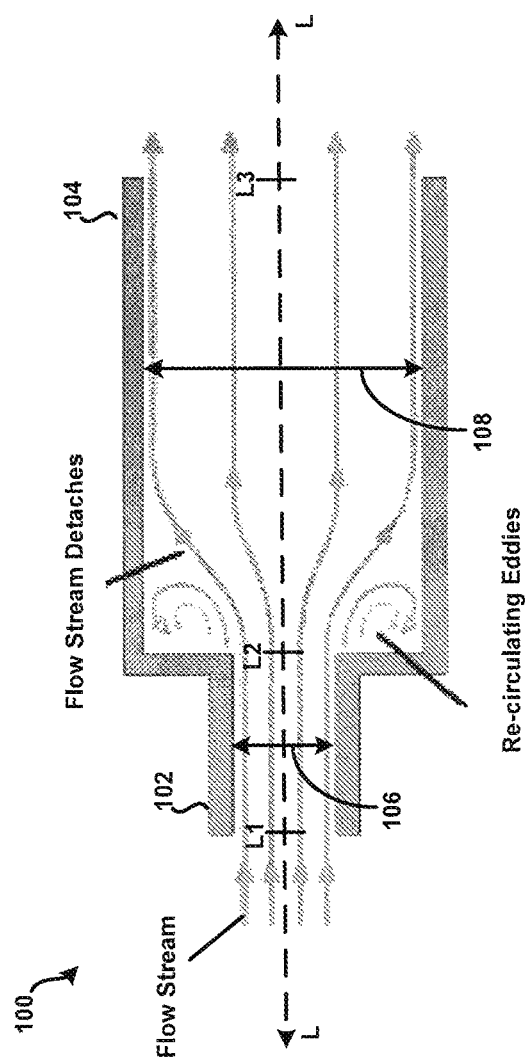
FIG. 1 shows a cross-section of a first example tubular body.

Referring now to FIG. 1, a cross-section of a first example tubular body 100 having an inlet 102 and a dispersion chamber 104 is shown according to the principles of the present disclosure. In this example, a fluid flow path of the inlet 102 is defined by a first internal diameter 106, and a fluid flow path of the chamber 104 is defined by a second internal diameter 108. Although shown approximately constant in FIG. 1, at least one of the first internal diameter 106 and the second internal diameter 108 may vary in dimension as defined with respect to a longitudinal axis L of the tubular body 100. Further, one or more apertures may be formed within the tubular body 100 at particular locations to allow a secondary air supply to enter the tubular body 100 during use to prevent or at least minimize the unintended accumulation or build-up of powder within the tubular body 100 for example the apertures 1310 in FIG. 13. Additionally, or alternatively, one or more internal surfaces of the tubular body 100 may be formed to exhibit rounded or curved features to prevent or at least minimize the unintended accumulation or build-up of powder within the tubular body 100. In addition to providing desirable fluid flow characteristics, as discussed further below, such configurable internal features or dimensions of the tubular body may be defined so as to provide for a draft angle for injection molding. In some embodiments, an injection molding technique or process may be used to fabricate at least the tubular body 100 of the present disclosure, including like features or elements discussed in further detail below. Other embodiments are possible.

For example, the first internal diameter 106 may taper inwardly, towards and as measured with reference to the longitudinal axis L, beginning approximately at a reference point L1 of the longitudinal axis L and ending approximately at a reference point L2 of the longitudinal axis L. Other embodiments are possible. For example, the first internal diameter 106 may taper inwardly towards the longitudinal axis L beginning approximately at the reference point L2, and ending approximately at the reference point L1. In another embodiment, the second internal diameter 108 may taper inwardly towards the longitudinal axis L beginning approximately at the reference point L3 and ending approximately at the reference point L2. Still other embodiments are possible.

For example, it is contemplated that an internal structural profile of at least one of the inlet 102 and the chamber 104 may be defined, as desired, such as to obtain or otherwise realize particular fluid flow characteristics within the tubular body 100. For example, as depicted in FIG. 1, the tubular body 100 may be arranged and configured such that a sudden flow stream expansion may occur when the relatively "small" cross-sectional fluid flow path of or defined by the inlet 102 opens abruptly into a "larger" cross-sectional fluid flow path of or defined by the chamber 104. In this example, high-energy forces may develop within the chamber 104. In one aspect, this may be due to relatively "low" pressure regions induced by relatively "high" velocity fluid entering the chamber 104, where a portion of the flow stream detaches and recirculation eddies may occur. Other mechanisms may contribute to the development of high-energy fluid flow within the chamber 104 as well. Further, such high-energy fluid flow, along with mechanical impact forces, may disrupt and aerosolize medicament powder agglomerates within the chamber 104 to provide for more effective deposition of medicament into the lungs of a patient. Still other embodiments of the example tubular body 100 are possible as well. For example, in some embodiments, a difference between the reference point L1 of the longitudinal axis L and the reference point L2 may approach zero (0). In this example, the tubular body 100 may consist only of the chamber 104. Here, instead of an "inlet tube," the tubular body 100 may consist of an "inlet hole".

Figure 16A:
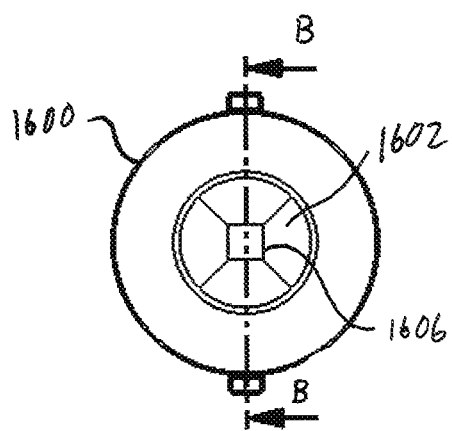
FIG. 16A shows a back view of non-circular inlet geometry.
Figure 16B:
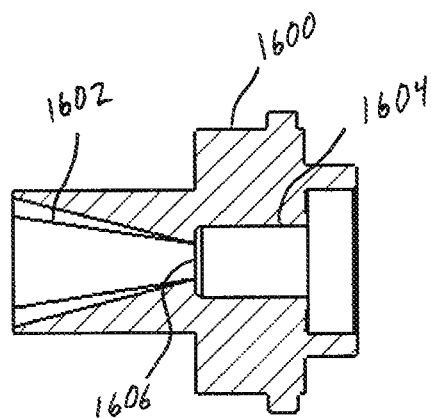
FIG. 16B shows a cross-section of the non-circular inlet geometry of FIG. 16A.

The geometry of the inlet to the dispersion chamber plays a critical role in the resistance of the inhaler. The resistance (R) is a relationship between the pressure drop across the device at a given flow and is defined as $$R = \frac{\sqrt{\Delta P}}{Q}$$

where $\Delta P$ is the pressure drop across the device (cm $H_2O$) and Q is the flow (LPM) at the given $\Delta P$. One embodiment includes a conical or conical frustrum inlet 1002 of FIG. 10. Experiments have shown that a conical frustrum inlet significantly reduces the resistance of the inhaler compared to a tube or inlet hole geometry. An experiment was conducted comparing different inlet geometries with the same inlet 106 and dispersion chamber diameter 108 as defined in FIG. 1: (1) conical frustrum inlet, (2) tubular inlet, and (3) inlet hole. The inlet diameter 106 was 2.72 mm and the chamber diameter 108 was 5.89 mm and a 4 mm spherical bead was used as the actuator. The length of the chamber from L2 to L3 as shown in FIG. 1 was 10 mm. The conical frustrum inlet was shown to have a significantly lower resistance than the tubular inlet and inlet hole design as shown in TABLE 1. The geometry of the inlet shape at reference point L2 in FIG. 1 can be non-circular in shape such as: triangular, square, polygon, or elliptical. For example, a first distal shape at L1 may taper to a smaller second proximal shape at L2. In some embodiments, the first shape and the second shape may be the same and in other embodiments the first shape and the second shape may be different. A tapering inlet with a square geometry at L2 is illustrated in FIG. 16A. FIG. 16A shows a front view of an inlet chamber 1602 and a dispersion chamber 1604 according to one embodiment. A distal opening of inlet chamber 1602 is shown as a circular opening, but may be any other shape. The inlet chamber 1602 tapers, as seen in the side cross-sectional view of FIG. 16B, to a smaller shape 1606 near the dispersion chamber 1604. Referring again to FIG. 16A, smaller shape 1606 may be any shape, such as a square, rectangle, circle, or triangle. Another experiment was conducted comparing the resistance of several different tapering inlets with varying geometries at reference point L2 in FIG. 1. The geometry at reference point L1 in FIG. 1 was a circle while the geometry at reference point L2 in FIG. 1 was varied to include an equilateral triangle, square, ellipse, and circle. The inlet area was held constant to match that of a circular inlet diameter of 3.30 mm which results in an open area of 8.55 mm². A 4 mm spherical bead was used as an actuator in the chamber, the chamber diameter 108 was 5.89 mm, and the length of the chamber was 10 mm for this test. The results are shown in TABLE 2, the square inlet had 10% lower resistance than the circular inlet. It was noted that the square inlet produced a similar audio sound from the actuator in terms of volume to the circular inlet. There may be added benefits to non-circular inlet shape designs to the dispersion chamber such as increased turbulence for better dispersion of powders. Lowering the resistance of the chamber is important because it increases the flow through the chamber for a given pressure drop. Increasing the flow may in turn increase the speed and/or frequency of the actuator oscillations which could be an important characteristic for efficient powder dispersion.

TABLE 1

| Geometry | Resistance (cm $H_2O$)$^{0.5}$/LPM |
| --- | --- |
| Conical Frustrum | 0.178 |
| Tubular | 0.242 |
| Inlet hole | 0.238 |

TABLE 2

| Inlet shape | Resistance (cm $H_2O$)$^{0.5}$/LPM |
| --- | --- |
| Circle | 0.131 |
| Equilateral triangle | 0.284 |
| Square | 0.115 |
| Ellipse | 0.122 |

Figure 2:
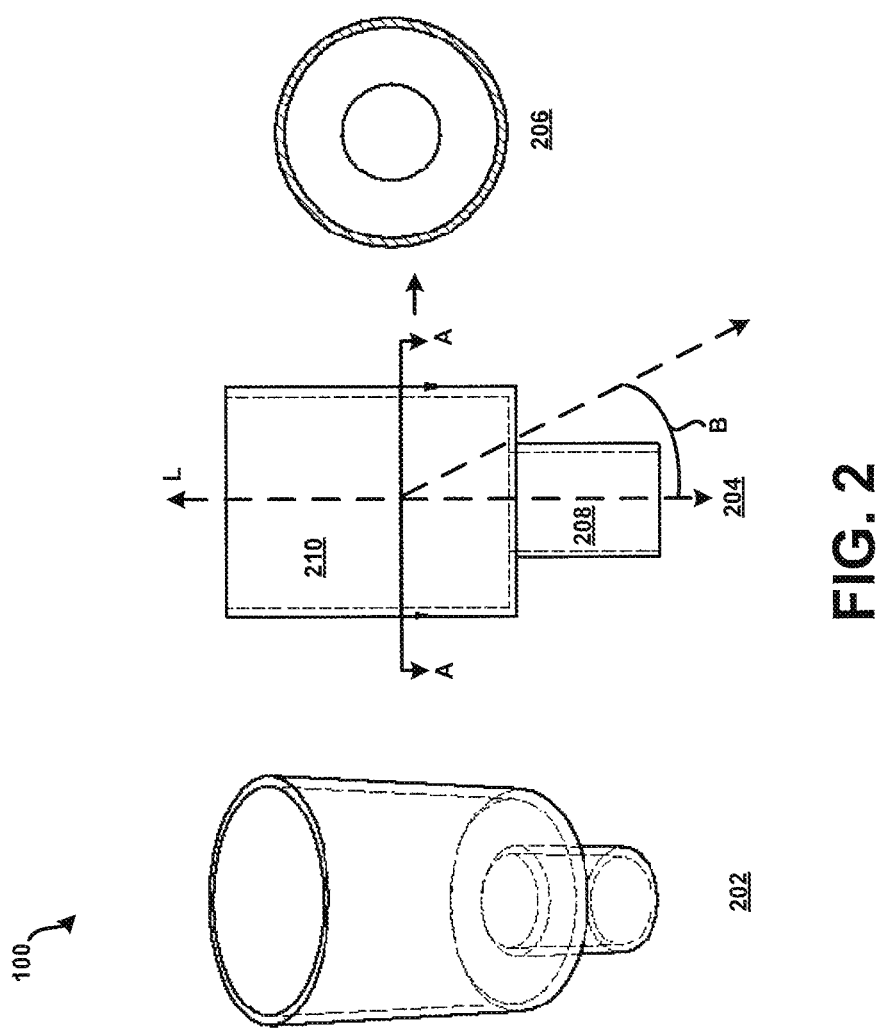
FIG. 2 shows the tubular body of FIG. 1 in multiple views.
Figure 25:
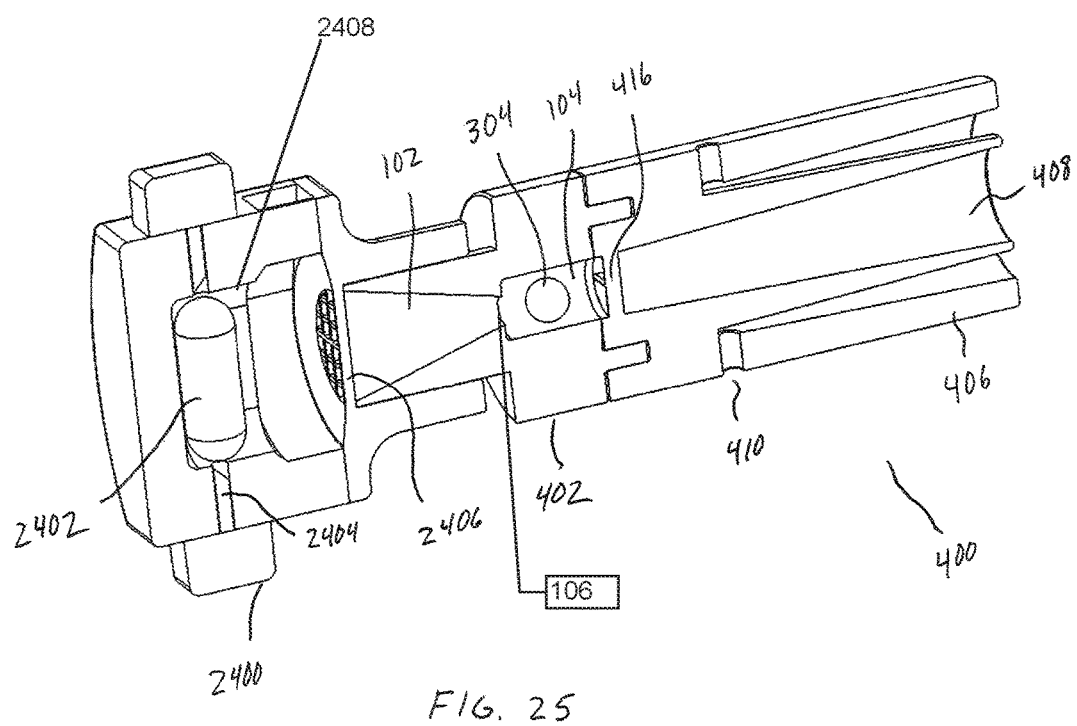
FIG. 25 shows a cross section of the DPI of FIG. 24.
Figure 28A:
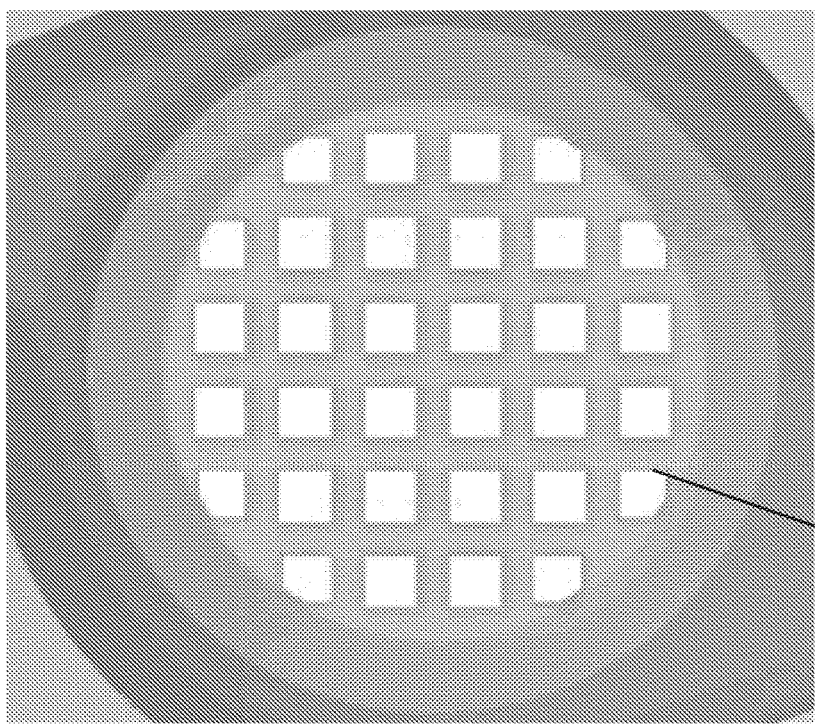
FIG. 28A shows a tightly-spaced grid structure used in experiment testing swirling flow according to embodiments.
Figure 28B:
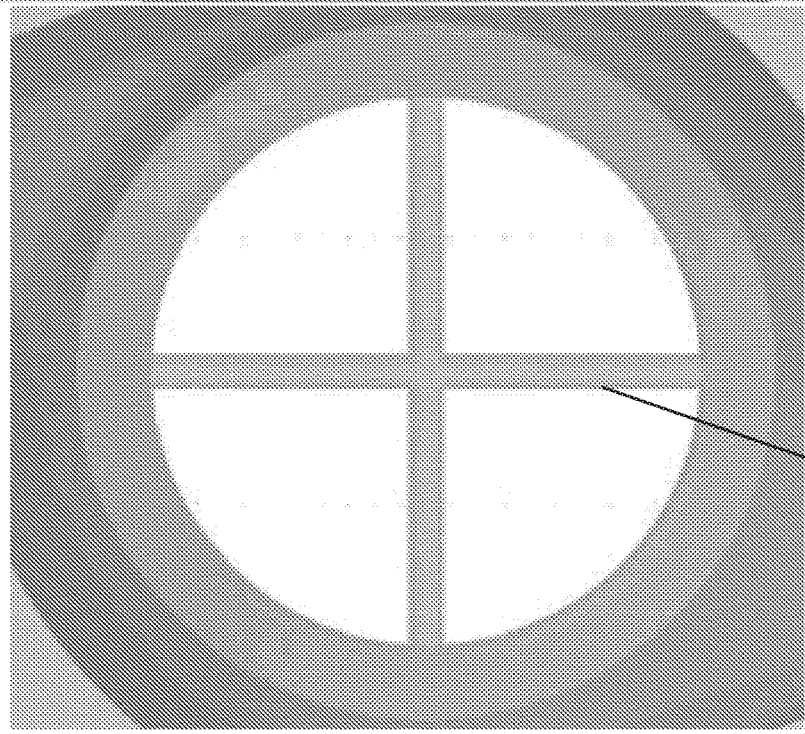
FIG. 28B shows a 2-piece grid structure used in experiment testing swirling flow according to embodiments.

Referring now additionally to FIG. 2, the tubular body 100 of FIG. 1 is shown in multiple views. In particular, the tubular body 100 of FIG. 1 is shown in perspective view 202, side view 204, and cross-section view 206. In this example, the cross-section view 206 is taken along an axis A-A of the side view 204. Additionally, and as illustrated in FIG. 1, the fluid flow path of or defined by the inlet 102 is coaxially aligned with the fluid flow path of or defined by the chamber 104. This is in contrast with a substantially "off-axis" alignment of the inlet 102 and the chamber 104, illustrated conceptually in FIG. 2 by a finite angle B defined with respect to the longitudinal axis L. A coaxial alignment may provide a number of advantages over such an "off-axis" alignment, such as facilitating or otherwise assisting in the development of high-energy forces within the chamber 104. The coaxial alignment may further enable the efficient transfer of powder into the chamber 104. However, other embodiments are possible. For example, in some embodiments, a central longitudinal axis of the inlet 102 may be at least slightly offset yet parallel to a central longitudinal axis of the chamber 104. Other benefits and/or advantages associated with the alignment of the inlet 102 and the chamber 104 may be understood from the preceding description provided in connection with FIGS. 1-2, and from the following description provided in connection with FIGS. 3-14. Although the inlet may be "off-axis" in alignment, the principal component of flow is in the axial direction. Furthermore, swirling or centrifugal flow into the inlet is detrimental to the oscillation of the bead. An experiment was performed using an embodiment as illustrated in FIG. 25. This embodiment has air inlets that are tangential to flow through the chamber 104 and they are shaped to induce a swirling or tangential flow which promotes capsule emptying. A grid is in place 2406 and it acts as a flow straightener similar to a honeycomb flow straightener. Two different grids were tested (1) a tightly-spaced grid 2800 of FIG. 28A and (2) simple 2-piece grid structure 2802 as shown in FIG. 28B. The tightly-spaced grid 2800 straightens and aligns the flow in axial direction similar to a honeycomb flow straightener used in wind tunnels. The tightly-spaced grid 2800 aligns the flow along the axis 204 shown in FIG. 2. The simple 2-piece grid 2802 provides little to no straightening of the flow. It was found that using the simple 2-piece grid 2802 prevented a spherical bead from oscillating under any flow conditions. The bead remained hovering near the inlet and did not oscillate.

Figure 3:
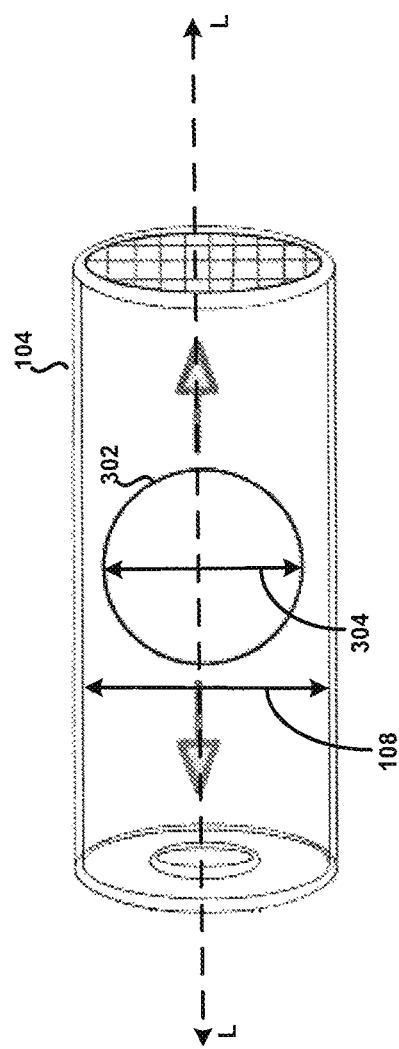
FIG. 3 shows a bead positioned within a chamber of the tubular body of FIG. 1.

For example, referring now additionally to FIG. 3, an actuator which could be shaped as a spherical bead 302 may be positioned within the chamber 104 of the tubular body 100 of FIGS. 1-2. In this example, the bead 302 may be approximately spherical, at least on the macroscale, and oscillate in a manner similar to that described in U.S. application Ser. No. 13/469,963, filed 11 May 2012, and entitled "Bead-Containing Dry Powder Inhaler," the complete disclosure of which is herein incorporated by reference. In some embodiments the actuator may be aspherical, or other shapes which may improve oscillation characteristics of the actuator. Further, a relationship between the diameter 304 of the actuator or bead 302, the first internal diameter 106 of the inlet 102, and the second internal diameter 108 of the chamber 104 may be of the form: $(d_{bead})^2 = (d_{inlet})(d_{chamber})$, where $d_{bead}$ and $d_{inlet}$ and $d_{chamber}$ are of similar order of magnitude. For example, in one embodiment $d_{bead}$ may be about 4.00 mm, $d_{chamber}$ may be about 5.89 mm, and $d_{inlet}$ may be about 2.72 mm within manufacturing tolerance. In this example, a length of the chamber 104, $l_{chamber}$, such as defined by a distance approximately between the reference point L2 and the reference point L3 of the longitudinal axis L (see FIG. 1), may be 2 to 3.5 times the diameter 304 of the bead 302.

In some embodiments, a diameter of the bead 302 may be within a range of about 0.5 mm to about 15 mm. In some embodiments, a preferred diameter of the bead 302 may be within a range of about 1.5 mm to about 6 mm. Still other embodiments are possible. In some embodiments, a preferred ratio of the internal diameter 106 of the inlet 102 to that of the chamber 104 ($d_{inlet}/d_{chamber}$) may be within a range of about 0.40 to about 0.66 with a preferred range of 0.46-0.60, and even more preferred range of 0.50-0.60 or 0.53-0.60. In some embodiments, it may be preferred that the length of the chamber 104, $l_{chamber}$, is about 2 times to about 5 times the diameter of the bead 302. In other embodiments, it may be preferred that the length of the chamber 104, $l_{chamber}$, is about 2 to about 3.5 times the diameter of the bead 302. In other embodiments, it may be preferred that the length of the chamber 104, $l_{chamber}$, is about 2 to about 2.5 times the diameter of the bead 302.

In example embodiments, the length of the chamber 104 may determine whether the actuator 302 freely oscillates, without physical interaction with ends of the chamber 104. Actuator oscillation that frequently impacts the chamber ends may not be desirable as it may generate particulate matter which can inhaled by the patient. In this manner, the length of the chamber 104 may facilitate free oscillation of the actuator 302. A substantially "freely" oscillating actuator 302 may even more effectively disrupt and aerosolize powder agglomerates within the chamber 104, as passed from the source, to provide for more effective deposition of medicament into the lungs of a patient.

For example, a study was performed to evaluate the length of the chamber 104 and to determine whether a particular length of chamber 104 would allow the actuator, a spherical bead 302, to "freely" oscillate within the chamber 104. In particular, using a device similar to the device 400, a spherical bead actuator of fixed diameter, about 4 mm, was used across the study. The length of the chamber however was varied as 1.5×, 2.0×, 3.0×, 3.5×, 4.0×, and 9.8× diameter of the bead. In this manner, the study included evaluating at least six different device configurations. In general, it was found that oscillation of the bead within the chamber was similar for lengths up to and including 3.5× diameter of the spherical bead, yet varied for lengths 4.0× and 9.8× diameter of the bead. For example, a similar flow rate through the device was needed to allow the spherical bead to "freely" oscillate within the chamber at least for chamber lengths of 2.0× and 3.0× diameter of the bead. However, a "higher" flow rate was needed to allow the bead to "freely" oscillate within the chamber for a chamber length of 4.0× diameter of the bead. Further the spherical bead did not appear to "freely" oscillate within the chamber for a chamber length of 9.8× diameter of the spherical bead, for any flow rate through the device. At this chamber length, the spherical bead may not be fully influenced by the negative pressure field formed at the inlet of the device by the airflow through the sudden diameter expansion. Other mechanisms may be possible as well.

In another example, a study was performed to evaluate the length of the chamber 104 and to determine whether a particular diameter of the spherical bead actuator 302, for a fixed length of the chamber 104, would allow the actuator 302 to "freely" oscillate within the chamber 104. In particular, using a device similar to the device 400, a chamber of fixed length and diameter, about 10 mm length and about 6 mm diameter, was used across the study. The diameter of the spherical bead however was varied as 3.7 mm, 4 mm, and 4.7 mm. In this manner, the study included evaluating at least three different bead configurations. In general, it was found that oscillation of the bead within the chamber for a 4 mm bead did "freely" oscillate within the chamber at a first particular flow rate. At this flow rate for this device configuration, a distinct audible sound produced by oscillation of the bead within the chamber may be observed. Operation and characteristics of the device 400 having a 4 mm bead diameter is discussed in further detail below.

Further, it was found that oscillation of the spherical bead within the chamber for a 3.7 mm bead did "freely" oscillate within the chamber 104 at or about the first particular flow rate. However, a flow rate greater than the first particular flow rate was needed to observe an audible sound similar to the distinct audible sound produced by oscillation of the spherical bead within the chamber for the 4 mm bead. Here, a greater flow rate may be required to produce the audible sound due to a reduced effective cross-sectional area of the 3.7 mm bead, as compared to the 4 mm bead. Other mechanisms may be possible as well. Further, it was found that oscillation of the bead within the chamber for a 4.7 mm bead did not "freely" oscillate within the chamber at or about the first particular flow rate. Here, the effective cross-sectional area of the 4.7 mm bead may be too large such as to prohibit "free" oscillation within the chamber. Other mechanisms may be possible as well.

Figure 17:
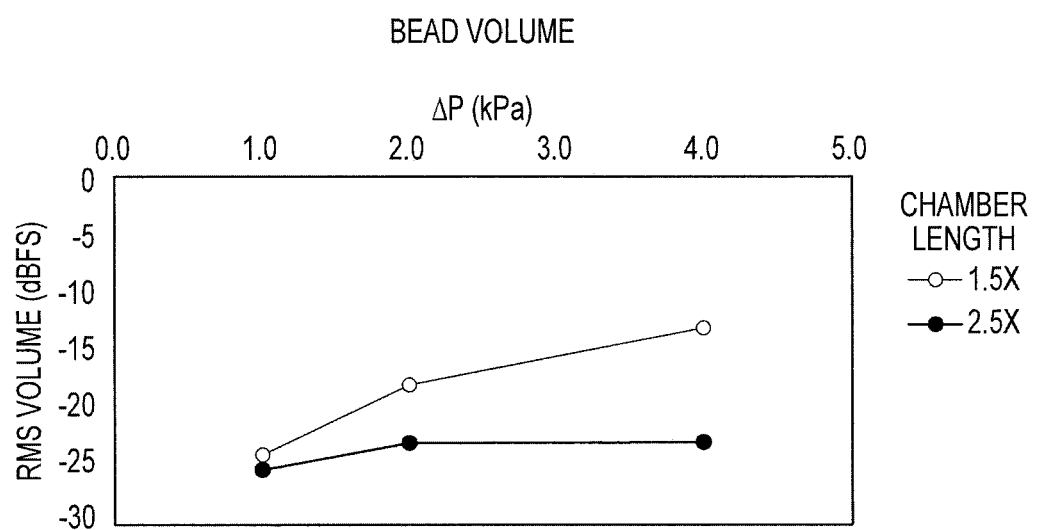
FIG. 17 bead sound level plot for different chamber lengths.
Figures 18A, 18B:
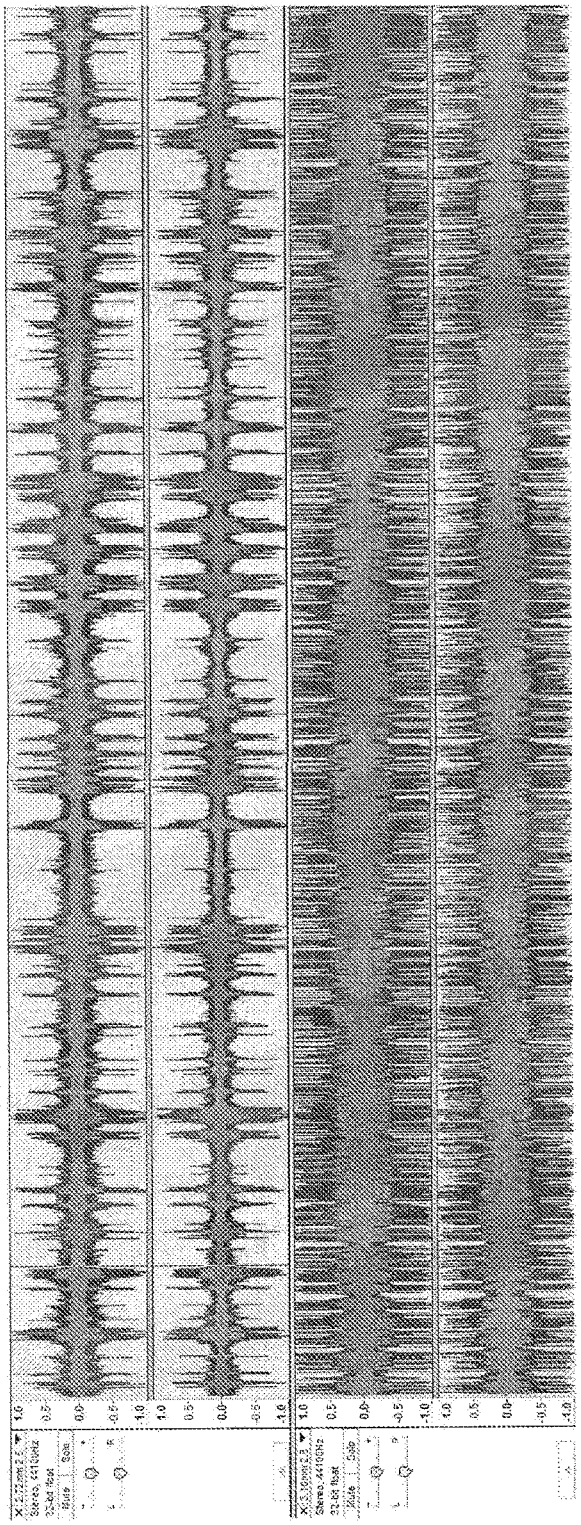
FIGS. 18A and 18B show a bead sound comparison for different inlet channel and chamber diameters.
Figure 19A:
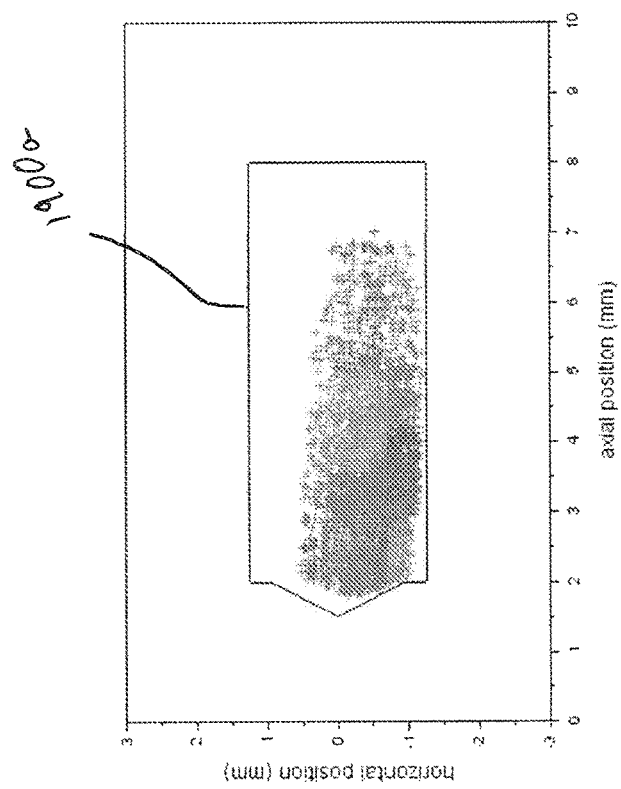
FIGS. 19A-19C show bead position plots to determine chamber end contact for inlet diameters of 2.72 mm.
Figure 19B:
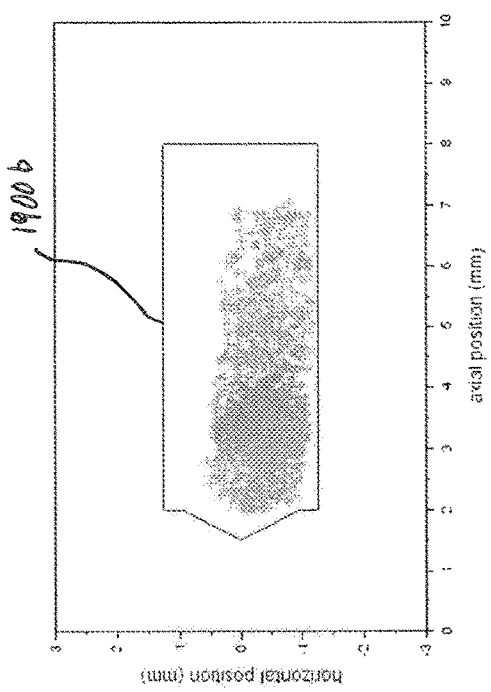
Figure 19C:
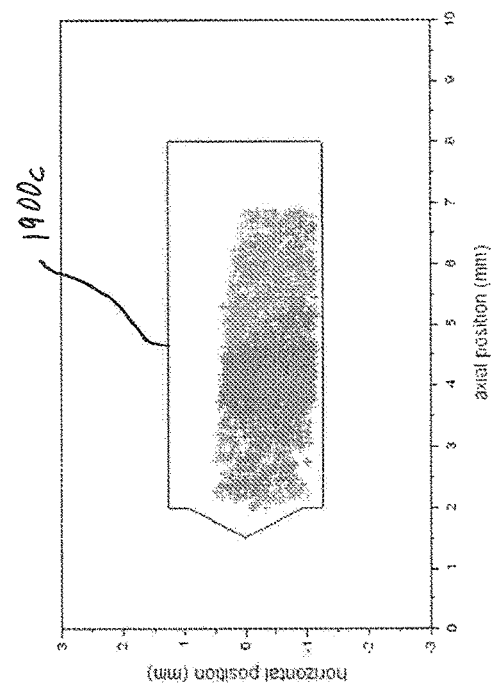
Figure 20B:
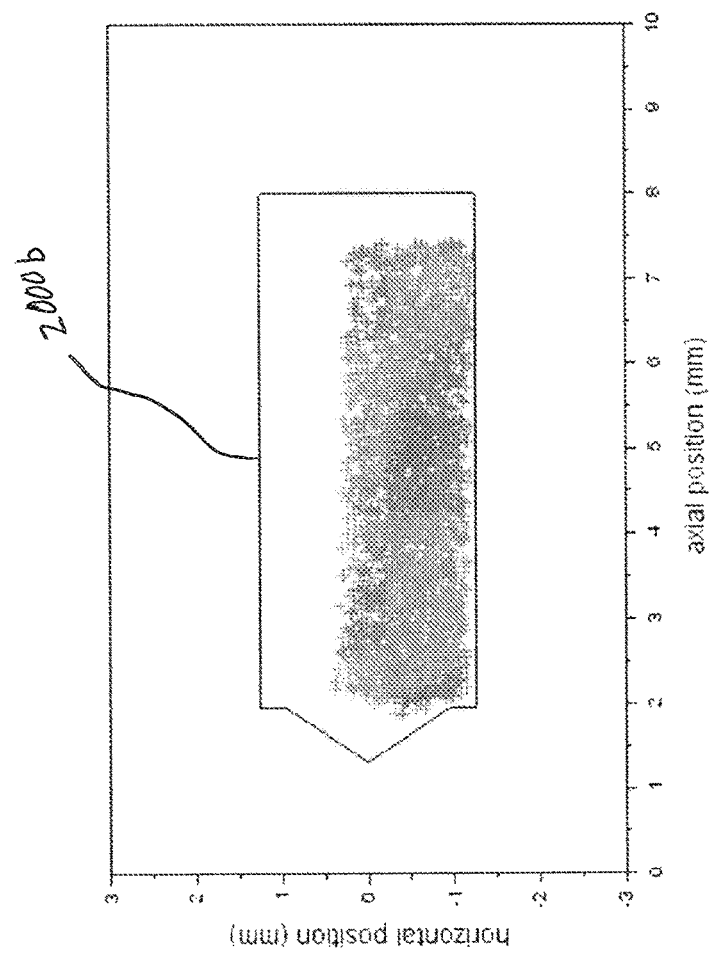
Figure 20C:
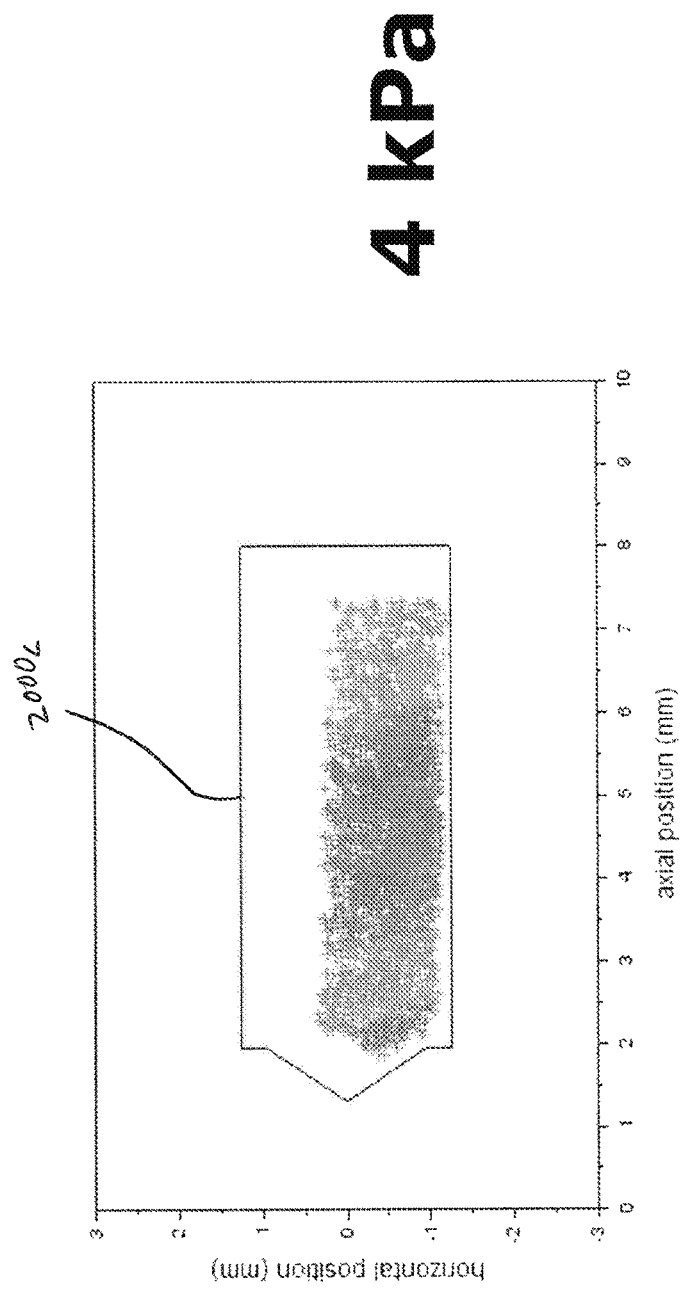

As described above, the actuator when oscillating can make an audible sound. The sound resulting from the oscillation of the actuator can be utilized as feedback to the user of the inhaler to confirm they have performed the inhalation maneuver correctly. In general the volume of actuator sound increases with flow, which can encourage the user to perform a deep forceful inhalation. The sound of the actuator is strongly related to the length of the chamber and the preferred range is 2.0-3.5× the bead diameter, with 2 to about 2.5× the diameter of the actuator 302 being most preferred. Experiments have shown that for chamber lengths less than 2.0× the actuator diameter the actuator oscillates freely but does not produce any significant sound. An experiment was performed to compare the sound from an oscillating bead with a chamber length of 1.5× and 2.5× bead diameter. The chambers for both used $d_{bead}$=4 mm, $d_{inlet}$=2.72 mm $d_{chamber}$=5.89 mm. The sound of 1.5 and 2.5× chamber length was recorded using a microphone and analyzed as shown in FIG. 17. The 2.5× chamber length produced an audible sound from bead oscillation from 1-4 kPa. The audible sound level in general increased with the pressure and flow through the chamber. The 1.5× chamber length showed minimal increase in audible sound from 1-4 kPa compared to the 2.5× chamber length. A further experiment was performed to evaluate the sound of a bead using different ($d_{inlet}/d_{chamber}$) ratios. Two chambers were tested with $d_{chamber}$=5.89 mm, and $l_{chamber}$=10 mm, one had an inlet diameter of 2.72 mm and the other 3.10 mm resulting in 0.46 and 0.53 ($d_{inlet}/d_{chamber}$) ratios respectively. The level of the audible sound resulting from the oscillating bead was recorded at 1, 2, and 4 kPa using a microphone. As shown in FIGS. 18A and 18B, the sound profile vs. time over roughly 20 seconds from the larger inlet ($d_{inlet}/d_{chamber}$=0.53) of FIG. 18B was both louder and more consistent at 1, 2, and 4 kPa. The smaller inlet to chamber ratio (0.46) of FIG. 18A showed significant periods of little sound resulting in an intermittent sound. A louder and more consistent sound is desirable for the audio feedback to the user. An intermittent sound such as that exhibited by ($d_{inlet}/d_{chamber}$)=0.46 may provide confusing feedback to the user as the sound is intermittent. The sound from bead oscillation could be used to provide valuable user feedback alerting the user that they have achieved the flow necessary for aerosol delivery. In some embodiments the sound of the bead could be analyzed by a microphone incorporated in the inhaler to determine if the patient reached a minimum flow rate for a period of time. This sound from the microphone could be processed and provide useful information to the patient and train them to achieve the necessary flow rate and time of inhalation for proper use of the inhaler. Furthermore this mechanism could be utilized as a patient compliance monitoring system to report when the inhaler was used and if the patient achieved the flow rate and volume necessary for powder delivery.

Continuing with the above dimensional example, the length of the chamber 104 may thus be about 10 mm for a 4 mm diameter bead. In this example, and when the ratio relationship between the diameters of the bead 302, the inlet 102, and the chamber 104 is observed, the bead 302 may oscillate within the chamber 104 generally without experiencing continuous physical collisions with either end of the chamber 104. An experiment was performed to determine the frequency of bead collision with the ends of the chamber. Two clear chambers were machined from acrylic for use with a 4 mm bead ($d_{chamber}$=5.89 mm, $l_{chamber}$=10 mm, $d_{inlet}$=2.72 mm and 3.10 mm) and the bead motion was recorded at 1200 frames/second for 5 seconds using a high speed camera. The video was analyzed to track the bead through the entire video. The center of the bead was plotted for all frames as seen in FIGS. 19A-C and FIGS. 20A-C. FIGS. 19A-C show pressure drops of 1, 2, and 4 kPa, respectively. FIGS. 20A-C show pressure drops of 1, 2, and 4 kPa, respectively. A polygon (1900*a-c* and 2000*a-c* in FIGS. 19A-C and FIGS. 20A-C, respectively) was drawn such that if the center of the bead was inside the polygon no contact is made with the ends of the chamber. It was found through high speed video observation bead never made contact with either end of the chamber from 1-4 kPa pressure drop for either inlet size. Such an arrangement may further facilitate development of high energy forces within the chamber 104 to more efficiently disrupt and aerosolize medicament powder agglomerates within the chamber 104 for more effective deposition of medicament into the lungs of a patient. Such an arrangement may further facilitate development of high energy forces within the chamber 104 to more efficiently disrupt and aerosolize medicament powder agglomerates within the chamber 104 for more effective deposition of medicament into the lungs of a patient.

In general, high-energy forces may refer to dispersive forces that may strip drug from the bead 302, and deaggregation or deagglomeration forces that may break-up or break-apart aggregates in powder fed into the chamber 104. Here, the terms deaggregation or deagglomeration, and aggregation or agglomeration may be used interchangeably. The high-energy forces may be generated by the bead 302 when rapidly oscillating within the chamber 104 via formation of turbulence and eddies within the chamber 104, compression and decompression zones within the chamber 104, and the like. In some instances the bead may be spinning on its axis as well as oscillating along the axial length of the chamber. This may more effectively disrupt and aerosolize powder agglomerates within the chamber through the Magnus effect exerted by the spinning bead. The Magnus effect is a generation of a sidewise force on a spinning cylindrical or spherical solid immersed in a fluid (liquid or gas) when there is relative motion between the spinning body and the fluid.

When a DPF (Dry Powder Formulation) is passed through the chamber 104 containing the bead 302, which is oscillating "rapidly" such as, for example, at a frequency greater than about 10 Hz, these high frequency oscillations of the bead 302 may produce high-energy forces within the chamber 104. This may disrupt agglomerates of drug particles that may be held together at least by cohesive forces, such as by van der Waals forces, static electrical forces, etc. Additionally, physical collisions between the bead 302, when rapidly oscillating, and potentially aggregated or agglomerated powder particles as they pass through the chamber 104 may promote de-aggregation of the agglomerates. The oscillation frequency may typically be between about 1 to about 1,000 Hz, and may preferably be between about 10 to about 500 Hz, although other frequencies may also occur. However, in some cases, the oscillation frequency could be up to about 2,000 Hz.

As mentioned above, the example bead 302 disposed within the example chamber 104 may oscillate in a manner similar to that described in U.S. application Ser. No. 13/469, 963, filed 11 May 2012, entitled "Bead-Containing Dry Powder Inhaler." However, in accordance with the present disclosure, the bead 302 may not include a pre-coated powder on its surface. Rather, powder may be separately introduced into the chamber 104 from a receptacle or powder storage element, such as dose containment or dosing chamber which can include but is not limited to capsules, reservoir, and blisters, or other temporary holding compartment or region, or from another dry powder inhaler, as described further below. With this configuration, the powder may be initially placed into a dose containment chamber. When a patient inhales from a mouthpiece, air may be drawn through the dose containment chamber which moves the powder into the chamber 104, where it encounters the bead 302 oscillating primarily along the longitudinal axis L (see e.g., FIG. 3).

In some embodiments, however, the bead 302 may be coated with drug. This may act as a detachment platform for the drug coated on its surface, as well as a dispersion mechanism for drug formulation located and introduced upstream of the bead. For example, for a combination drug product, such as delivering two or more drugs in a single inhalation maneuver, where one drug is delivered in a larger dose, such as an inhaled corticosteroid, than the other drug, such as a long-acting beta-agonist, the lower dose drug may be coated onto the surface of the bead 302, while the larger dose drug is located in a dose containment container, such as a capsule, blister, reservoir, etc., upstream of the chamber 104 containing the drug-coated bead. Thus, during inhalation, oscillation of the bead 302 may serve as a detachment platform to the drug adhered to its surface, and as a dispersion mechanism to the powder that is located upstream.

Additionally, the bead 302 may be coated with a layer of durable material. An example of such a material may include, but is not limited to, gelatin, sugars, any pharmaceutically acceptable film coating materials, including polymers, metallic coatings, anti-static coatings, plasma coatings, etc. This may be beneficial for example when bead material can erode or fragment. In this example, the layer thickness may depend on the density of the material to be added, such that the addition of the coated layer does not eliminate or substantially impair or inhibit the ability of the bead 302 to oscillate within the chamber 104. The bead may have various surface finish ranging from Ra (μm) 0.012-50, where $R_a$ is the average surface roughness. The surface finish may affect bead motion and in turn may improve the dispersion and aerosolization of powder agglomerates within the chamber.

Using the bead 302 as a dispersion mechanism may provide a number of advantages. For example, by employing the oscillating bead in a chamber in the capacity of a dispersion engine, large doses such as, for example, about 1 mg to about 25 mg or greater, may be delivered by delivering them in capsule or blister or reservoir dose containers. However, it will be appreciated that smaller doses may also be delivered. For example, doses greater than about 1 μg of active drug may be delivered. In some cases, the active drug may be blended with a carrier, such as lactose. Also, when the bead 302 is not coated with drug and used as a dispersion mechanism, there is no retention mechanism required to hold the bead 302 tightly within the inhaler, decreasing the complexity of the DPF. Still further, using the bead 302 as a dispersion mechanism may require no additional or complicated processing steps for the DPF formulations, as the powder may be produced by traditionally employed methods, particle engineered formulations may also be used.

Additionally, the bead 302 in the present disclosure may oscillate generally within the center of the chamber 104, along the longitudinal axis L, where physical contact between the bead 302 and inner walls of the chamber 104, and possibly ends of the chamber 104, may occur infrequently, if at all. This type of dispersion mechanism may be beneficial as collisions between walls of the chamber 104 and the bead 302 could serve to rub powder onto either the surface of the bead 302 or inner walls of the chamber 104 when powder is caught there during a physical collision, thereby decreasing an amount of powder available for transfer into the lungs of a patient. Alternatively the frequent collision of the bead 302 with the walls of the chamber 104 may act to scrub off any drug adhered to the wall(s), thus increasing an amount of powder available for transfer into the lungs of a patient.

Referring still to FIGS. 1-3, and as mentioned above, alignment of the inlet 102 and the chamber 104, may provide significant advantages over inhalers having an "off-axis" alignment. In particular, the tubular body 100 of the present disclosure may produce an approximately symmetrical flow stream expansion that drives oscillation of the bead 302. Such a configuration may enable a powder dispersion device, or dry powder inhaler, incorporating aspects of the tubular body 100, to be constructed with minimal bulk. For example, the chamber 104 in example embodiments of the present disclosure may be modeled as a cylinder of the dimensions detailed above (e.g., $d_{chamber}$~5.89 mm, $l_{chamber}$~10 mm) for a similar 4 mm bead. Accordingly, a maximum volume occupied by the chamber 104 is about 272 cubic mm based on the expression $V_{cylinder}=\pi r^2 l$.

Referring now to FIGS. 4-5, an example powder dispersion device or inhaler 400 is shown in accordance with the principles of the present disclosure. In particular, FIG. 4 shows a first view of the device 400 of FIG. 4 in cross-section. FIG. 5 shows a perspective view of the device 400 of FIG. 4. The device 400 may generally incorporate aspects of the example tubular body 100 described above in connection with FIGS. 1-3. Additionally, or alternatively, the device 400 may generally incorporate aspects of one or more of the tubular bodies described below in connection with FIGS. 10-14. For example, the device 400 may include a first housing 402 comprising the inlet 102 and the chamber 104 of the tubular body 100. Additionally, although not expressly shown, the bead 302 may be positioned within the chamber 104, such as shown in FIG. 3. The device 400 may further include a second housing 404 comprising a sheath flow channel 406 that surrounds and is not in fluid connection with a primary or main powder flow channel 408. In some embodiments, the first housing 402 may be integrally formed with the second housing 404. In one embodiment, the chamber 104 and the main powder flow channel 408 may have at least one common structural dimension, such as internal diameter for example. Additionally, the second housing 404 may itself comprise of, be coupled to, or otherwise incorporated within, a mouthpiece adapted to be placed within the mouth of a patient, or in a nasal adapter adapted to conform to the nostrils of a patient. The device 400 may further include a plurality of flow bypass channels 410 that are formed within the second housing 404. The flow bypass channels 410 may be in fluid connection with the sheath flow channel 406.

The device 400 may further include a dosing chamber 412, a retaining member 416, and a piercing member 418 disposed at an end of the chamber opposite the inlet 102. The piercing member 418 may puncture or otherwise perforate a capsule, blister, or powder reservoir 414 as arranged or positioned within the dosing chamber 412. In general, the retaining member 416 may include at least one opening or aperture sized to permit air and powdered or otherwise aerosolized medicament to pass through the retaining member 416, and to prevent the possibility of the bead 302 from exiting the chamber 104. At least one opening or aperture may, in some embodiments, be arranged and configured (e.g., diameter, pattern, symmetry, etc.) to maintain desired air flow characteristics with the device 400, such that the bead 302 may disrupt and aerosolize medicament powder agglomerates within the chamber 104 to provide for more effective deposition of medicament into the lungs of a patient.

Figure 4:
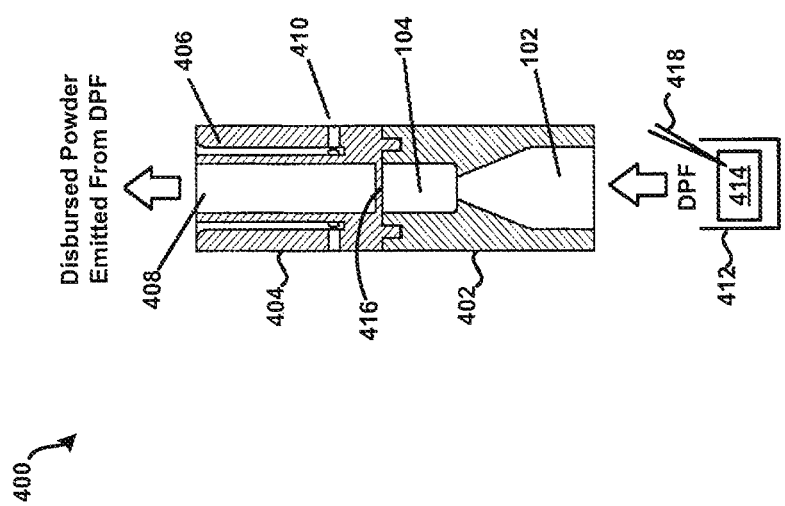
FIG. 4 shows a first view of an example powder dispersion device in cross-section.

In one example, referring specifically to FIG. 4, a patient may prime the device 400 by puncturing the capsule, blister, or transfer of a dose from a powder reservoir 414, and then inhale, drawing air through the chamber 104 which in turn draws the DPF from the dosing chamber 412 into the adjacent chamber 104 via the inlet 102, where the bead 302 is rapidly oscillating, creating high-energy forces that may strip drug from the surface of carrier particles in the DPF, or when the bead 302 is drug-covered, and/or de-agglomerate drug powder aggregates and drug-on-drug aggregates. Drug particles may then be deposited in lungs and airways of a patient from the primary or main powder flow channel 408 based on direction of air flow through the device such as shown in FIG. 4. Such a "self-dosing" scenario may be useful for effectively dispensing both traditional binary or ternary DPF formulations, drug and carrier/excipient particles, and pure drug-powder formulations where there are no carrier particles are present. Other embodiments having similar effects are possible, as discussed further below.

Figure 5:
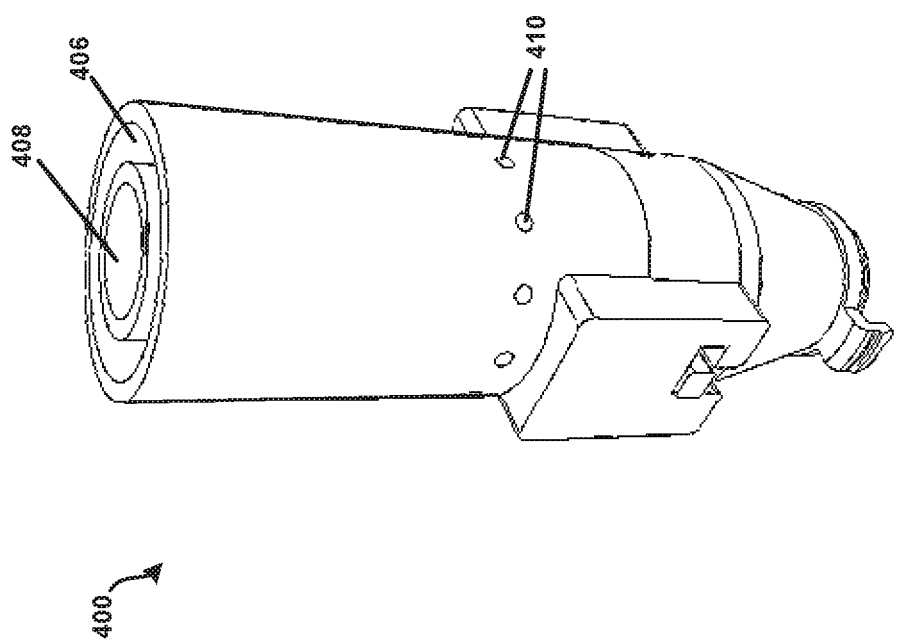
FIG. 5 shows a perspective view of the device of FIG. 4.

In general, the resistance to flow of the device 400 may be adjusted by altering the geometry and/or arrangement of at least one of the inlet 102, the bead 302, the sheath flow channel 406, the main powder flow channel 408, and the flow bypass channel(s) 410. Additionally, as shown in FIG. 5, the flow bypass channels 410 may be located radially around the body of the second housing 404, and fluidly connected to the sheath flow channel 406. In some embodiments however, the device 400 may not include any flow bypass channels. In one embodiment, the flow bypass channels 410 may comprise a bypass channel where air is drawn into it via multiple individual side holes or channels located radially around the body of the second housing 404. However, other embodiments are possible. For example, the flow bypass channels 410 may comprise of different numbers and diameters of individual channels and entry points into the sheath flow channel 406. Further, one or more of the flow bypass channels 410 may be parallel through the main powder flow channel 408, or may be in fluid connection with, and then diverge from, the main powder flow channel 408. Still other embodiments are possible.

One or more of the bypass channels 410 may be "opened" or "closed" such as by removal or insertion of a resilient material therein to "unplug" or "plug" the same. This may result in changes in the overall resistance of the device 400, thereby influencing flow rate through the device 400. For example, a person may inhale through a "high" resistance inhaler with a lower inspiratory flow rate than they would through a "low" resistance inhaler, despite inhaling with the same inhalation effort. In this manner, the device 400 may be "tuned" to respond "optimally" to the needs of a patient. In other words, the device 400 in accordance with the present disclosure may be tailored to suit particular patient needs. For example, resistance of the device 400 may be approximately inversely proportional to diameter of the bead 302.

Thus, for a "larger" diameter bead 302, one or more of the flow bypass channels 410 may be "closed" to increase resistance of the device such that a patient may receive a proper dose of medicament irrespective of possibly diminished inhalation capacity. Further, it is contemplated that the flow bypass channels 410 when "opened" may at least partially prevent or at least minimize the accumulation or build-up of powder in areas where non-laminar flow, such as flow eddies for example, may be present. Various other possible configurations or arrangements for such housing apertures are described in further detail below in connection with at least FIGS. 10-14.

Figure 6:
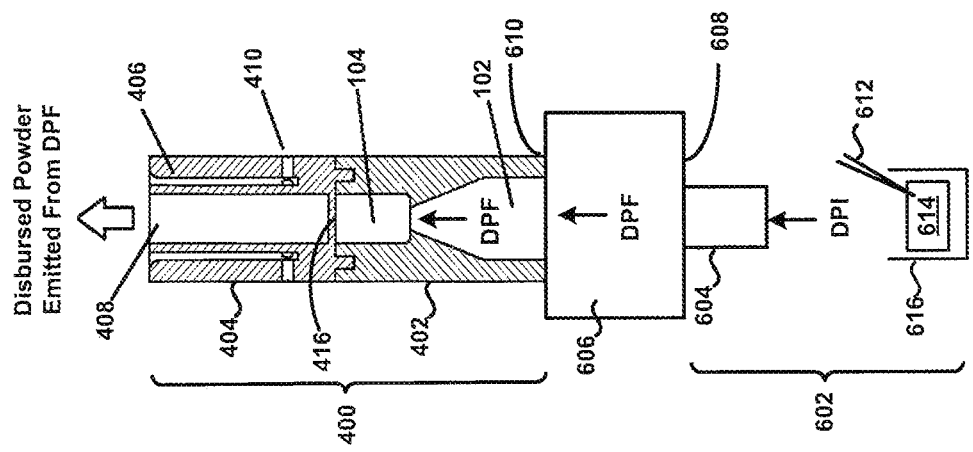
FIG. 6 shows a second view of the device of FIG. 4 in cross-section.

Referring now to FIG. 6, a second view of the device 400 of FIG. 4 is shown in cross-section. In this example, the device 400 is coupled to a mouthpiece 604 of an inhaler 602 by a coupling 606, thereby allowing powder to flow through the inhaler 602 as during "normal" operation, and then into the chamber 104 containing the bead 302 (see also FIG. 3). In particular, a piercing member 612 may puncture or otherwise perforate a DPF containing capsule, blister, or powder reservoir 614 as contained within a dosing chamber 616 of the inhaler 602. Powder may then be caused to flow through the inhaler 602 into the chamber 104 containing the bead 302 via the mouthpiece 604 and coupling 606. The bead 302 may then disrupt and aerosolize DPF powder agglomerates within the chamber 104 to provide for more effective deposition of medicament into the lungs of a patient in a manner such as described above.

In general, the coupling 606 may be a rigid or flexible coupling formed of any material, or combination thereof, such as thermoplastic/thermosetting plastics, metals, glasses, elastomers, etc., and may be coupled to the mouthpiece 604 of the inhaler 602 on a first end 608, and to the device 400 on a second end 610. Here, it may be preferred that the material has surface properties that minimize the attraction of powder particles. The coupling 606 may be permanently fastened to, such as being integrally formed therewith, at least one of the inhaler 602 and the device 400, or may be removable fastened with least one of the inhaler 602 and the device 400. For example, the coupling 606 may be fastened to the inhaler 602 by one of a "snap-fit" or a "pressure-fit" or a "twist-to-fit" mechanism, etc., such as in a "quick" connect/disconnect implementation. Still other embodiments are possible. For example, it will be appreciated that the device 400 may not be limited to being "clipped" or otherwise "coupled" to other inhalers. Further, aspects of the present disclosure may be used in combination with any type of DPF dose containment system, and may not be limited to a capsule, blister, or reservoir dose containment systems.

As discussed above in connection with FIG. 4, a patient may prime the device 400 by puncturing the capsule, blister, or powder reservoir 414, and then inhale, drawing the powder from the dosing chamber 412 into the adjacent chamber 104 via the inlet 102, where the bead 302 is rapidly oscillating, creating high-energy forces that may strip drug from the surface of carrier particles (e.g., when the bead 302 is drug-covered), and/or de-agglomerate powder aggregates. Drug particles may then be deposited in lungs and airways of a patient from the primary or main powder flow channel 408 based on direction of air flow through the device such as shown in FIG. 4. Such a "self-dosing" scenario may at least be useful for effectively dispensing both traditional binary or ternary DPF formulations, drug and carrier/excipient particles, and pure drug-powder formulations where there are no carrier particles are present. Other embodiments are however possible.

Figure 7:
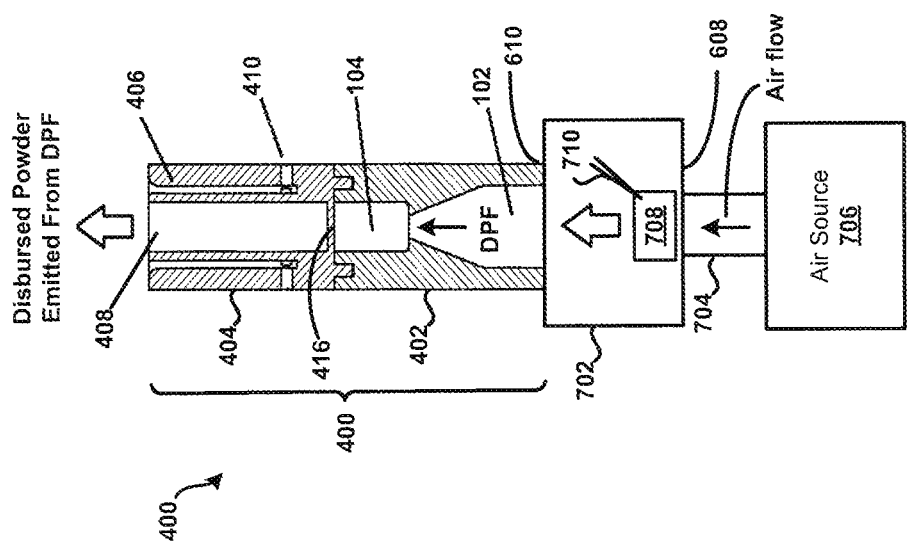
FIG. 7 shows a third view of the device of FIG. 4 in cross-section.

For example, referring now specifically to FIG. 7, a "forced-dosing" scenario is described in accordance with the present disclosure. In particular, a third view of the device 400 of FIG. 4 is shown in cross-section in FIG. 7. In this example, a coupling 702 is shown that is removably coupled to the first housing 402 of the device 400. The coupling 702 includes an inlet 704 that is removably coupled to an air source 706. In one embodiment, an individual other than a patient may prime the device 400 by puncturing a capsule, blister, or reservoir 708 of the coupling 702 using a piercing member 710. The source 706 may then be employed to force air through the device 400, drawing powder from the reservoir 708 into the adjacent chamber 104 via the inlet 102, where the bead 302 is rapidly oscillating, creating high-energy forces that may strip drug from the surface of carrier particles (e.g., when the bead 302 is drug-covered), and/or de-agglomerate powder aggregates. Drug particles may then be deposited in lungs and airways of the patient from the primary or main powder flow channel 408 based on direction of air flow through the device such as shown in FIG. 7.

Such a "forced-dosing" scenario may beneficial when, for example, emergency treatment of unconscious or otherwise unresponsive personnel may be necessary. For example, the device 400 may enable a responder to administer treatment agent to the lungs of a patient. Additionally, the second housing 404 may itself comprise of, be coupled to, or otherwise incorporated within, a mouthpiece adapted to be placed within the mouth of a patient, or in a nasal adapter adapted to conform to the nostrils of a patient. In the example of FIG. 7, the second housing 404 of the device 400 may be securely positioned within or on the mouth or nasal passages of a patient. With air expelled from the lungs of a responder into the inlet 604, the device 400 may be activated or actuated such as to deposit a treatment agent into the lungs and airways of the patient. In this example, the source 706 corresponds to the lungs of an individual. Other embodiments are possible. For example, in some embodiments the source 706 may comprise of a ventilation bag, mechanical ventilator, mechanical pump, etc. Still other embodiments are possible.

At least FIG. 6-7 illustrate a scenario in which the example device 400 is coupled to, or fitted onto, an external feature of a dose containment system or powder source. Other embodiments are however possible. For example, referring now to FIG. 8, a scenario is illustrated in which the example device 400 is coupled to, or fitted onto, an internal feature of a dose containment system or powder source. In particular, the device 400 may replace a powder dispersion mechanism internal to an existing inhaler. An example of an existing inhaler may include the HandiHaler®, Twisthaler®, Turbuhaler®, Novolizer®, Plastiape RS01®, Turbospin® dry powder inhalers and others. Other embodiments are possible.

For example, a typical dose containment system or powder source 712 may generally include a dose module 714 that holds a portion of DPF, a powder dispersion module 716, and a mouthpiece module 718 that would in practice be used to deliver a dose of the DPF to a patient. In general, the powder dispersion module 716 may exhibit a tortuous path the DPF needs to navigate between its introduction into the flow path and release from the mouthpiece module 718. The tortuous path may possibly deaggregate DPF aggregates to some degree, but may also add flow resistance. In accordance with the principles of the present disclosure, the dose containment system or powder source 712 may be modified to replace the powder dispersion module 716 with the device 400, or subassemblies of the device 400, including an inlet, chamber with a bead, and an outlet similar to the device 400. Further, this may or may not include the second housing 404 of the device 400, where an existing element of an inhaler being modified may instead be used. In this example, the device 400 may enhance the efficiency of de-aggregation of DPF of the dose containment system or powder source 712, and may lower the resistance to flow within the dose containment system or powder source 712. Other benefits and advantages are possible as well.

Figure 9:
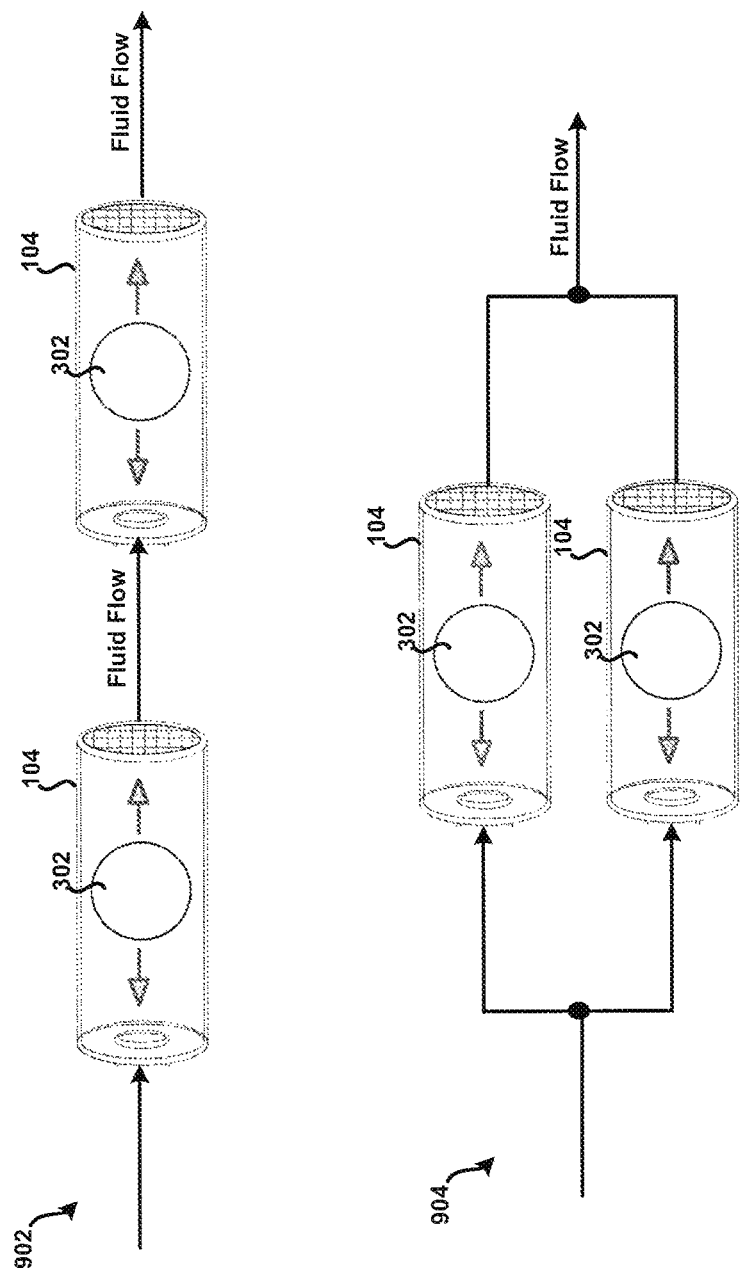
FIG. 9 shows the device of FIG. 4 in multiple configurations.

Referring now to FIG. 9, a simplified, conceptual, example schematic diagram of the example device 400 of FIG. 4 in multiple configurations is shown. In particular, the chamber 104 of the device 400 is shown in a series configuration 902 with another chamber 104, and in a parallel configuration 904 with another chamber 104. In this example, it is contemplated that multiple drugs in each their own (e.g., two or more) dispersion chambers (e.g., in addition to other elements of the example device 400 as desired) configured in accordance with the principles of the present disclosure may be coupled in series or parallel. Further, it is contemplated that any desired series/parallel combination may also be formed. For example, the series configuration 902 may be coupled in series with the parallel configuration 904. In another example, the parallel configuration 904 may be coupled in series with a single particular chamber 104, and etc.

In addition, it is contemplated that the type and configuration of the bead 302 may vary in the context of FIG. 9. For example, when multiple ones of the chamber 104 are connected in series and/or parallel, one or more of the respective dispersion chambers may have similar bead sizes, different bead sizes, similar bead materials, different bead materials, and etc. Further, it is contemplated that any desired series/parallel combination may be formed. In general, type and configuration of the bead 302 may vary as desired.

Such an implementation may be beneficial in many respects. For example, for combination therapies, one drug may pass through a particular dispersion chamber and another other drug may pass through a separate dispersion chamber, or both drugs can pass through the same dispersion chamber. Additionally, "downstream" of the dispersion chambers may merge into a single dispersion chamber, or be kept separate throughout the length of the device 400, such that the powders do not mix until they are emitted from the device. Still other benefits and/or advantages are possible as well.

Figure 10:
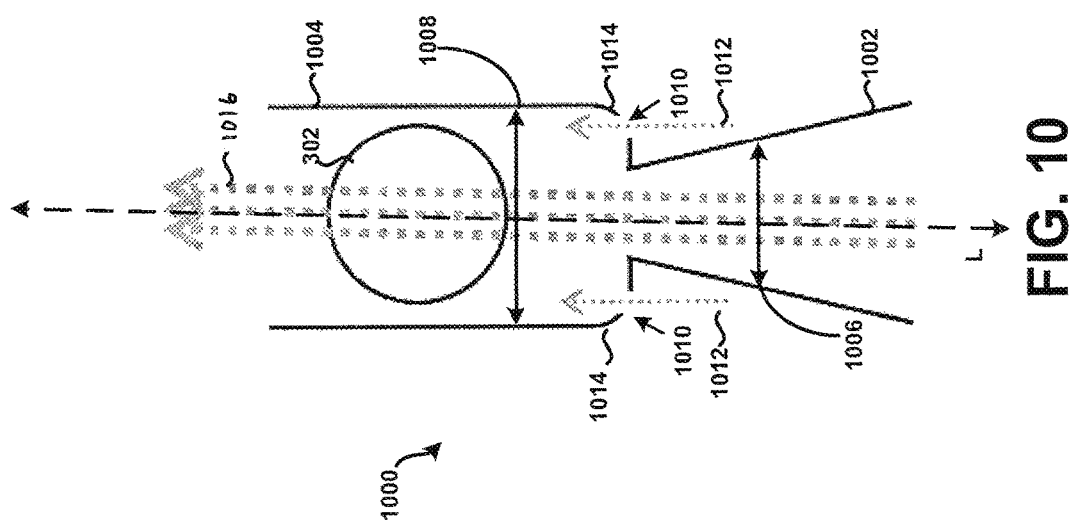
FIG. 10 shows a cross-section of a second example tubular body.

Referring now to FIG. 10, a cross-section of a second example tubular body 1000 having an inlet 1002 and a dispersion chamber 1004 is shown according to the principles of the present disclosure. In many aspects, the second example tubular body 1000 is similar to at least the tubular body 100 of FIG. 1. For example, a fluid flow path of the inlet 1002 is defined by a first internal diameter 1006 that varies or tapers along a longitudinal axis L, and a fluid flow path of the dispersion chamber 1004 is defined by a second internal diameter 1008. Further, one or more apertures 1010 are formed within the tubular body 1000 at particular locations to allow a secondary supply of air or air flow 1012 (sometimes referred to as "chase air") to enter the tubular body 1000 during its use, to prevent or at least minimize the unintended accumulation or build-up of powder within the tubular body 1000. In particular, it will be appreciated that air flowing through the one or more apertures 1010 may advantageously prevent or at least minimize the unintended accumulation or build-up of powder within internal edges or corners 1014 of the tubular body 1000 that are substantially adjacent the inlet 1002, because the force of that air would push powder away from the corners 1014 into the primary air stream 1016 for subsequent deposition into the lungs of a patient in a manner similar to that as discussed above. Among other things, this may advantageously increase the efficiency of powder deposition into the lungs of a patient, prevent build-up of powder that can dislodge in subsequent uses of the chamber as a multi-dose inhaler device resulting in a super-dose to be delivered to the patient, and/or prevent undesired waste of powder.

Figure 14:
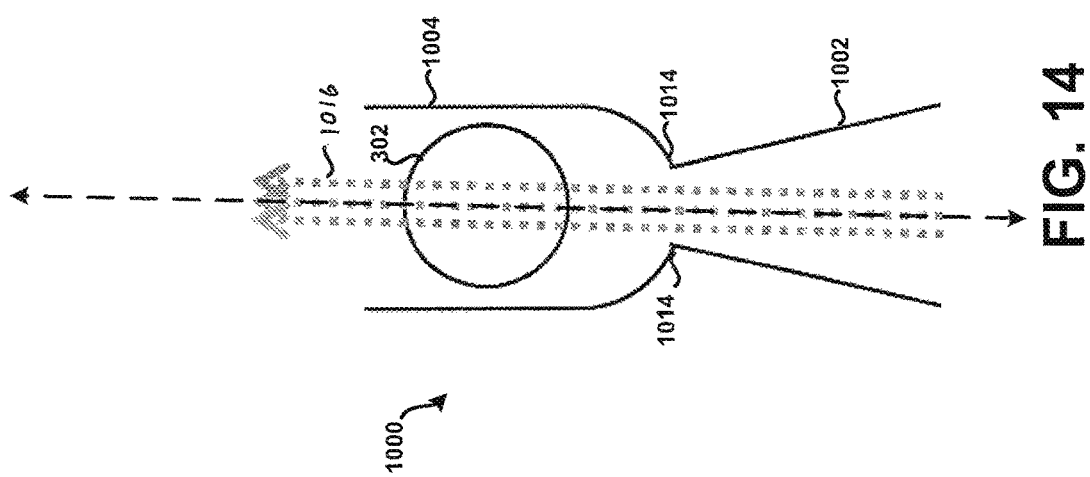
FIG. 14 shows a cross-section of a sixth example tubular body.
Figure 15:
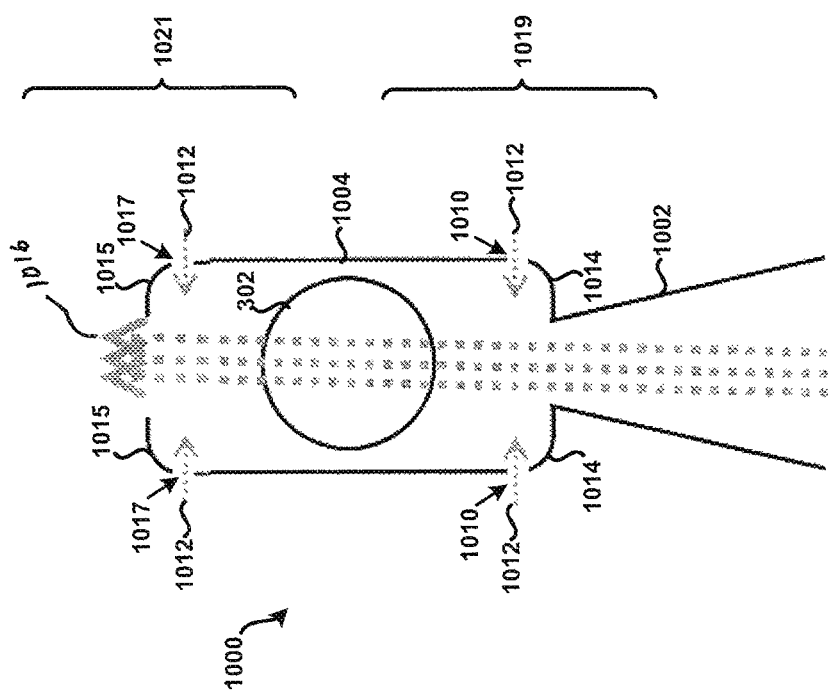
FIG. 15 shows a cross-section of a seventh example tubular body.

Additionally, or alternatively, the corners 1014 of the tubular body 1000 may be formed to exhibit rounded or curved surfaces to prevent or at least minimize the unintended accumulation or build-up of powder within the tubular body 100. FIG. 14 in particular shows the corners 1014 of the tubular body 1000 formed to exhibit rounded or curved surfaces, without the apertures 1010. Other embodiments are possible. For example, FIG. 15 in particular shows corners 1015 of the tubular body 1000 that are formed to exhibit rounded or curved surfaces on an end of the tubular body 1000 opposite corners 1014. Further, apertures 1017 are formed within the tubular body 1000 near or adjacent the corners 1015. It is contemplated that any feature or element discussed as being near or adjacent the inlet 1002 may additionally, or alternatively, be formed on an end of the tubular body 1000 opposite of the inlet 1002, such as shown in FIG. 15. This principle is applicable to each respective tubular body discussed in the context of the present disclosure. Further, the configuration and particular geometry of the corners 1015 and/or the apertures 1017 need not necessarily be the same as that exhibited by the corners 1014 and/or apertures 1010. For example, the tubular body 1000 as shown in FIG. 15 may have a first portion 1019 configured similar to that shown in FIG. 12, whereas a second portion 1021 may be configured as shown in FIG. 15. Still many other embodiments are possible.

It will be appreciated that such rounded or curved surfaces may more effectively prevent powder from accumulating or adhering to portions of the corners 1014 when compared to other profiles that have a sharp transition between surfaces, such as the stepped-edge profile shown in FIG. 1. In addition to providing desirable fluid flow characteristics, one or both of the apertures 1010 and the rounded corners 1014 may further facilitate efficient and effective fabrication of the tubular body 1000 by injection molding for example.

In the example of FIG. 10, the secondary air flow 1012 comprises air flowing through the apertures 1010 and into the dispersion chamber 1004 in a substantially or approximately parallel direction to the primary air stream 1016. Many other embodiments are possible. For example, referring now to FIG. 11, a cross-section of the second example tubular body 1000 is shown whereby the apertures 1010 are formed such that the secondary air flow 1012 comprises air flowing through the one or more apertures 1010 and into the dispersion chamber 1004 in a substantially or approximately perpendicular direction to the primary air stream 1016. The benefits associated with the secondary air flow 1012 are similar to that described above in connection with FIG. 10.

Figure 11:
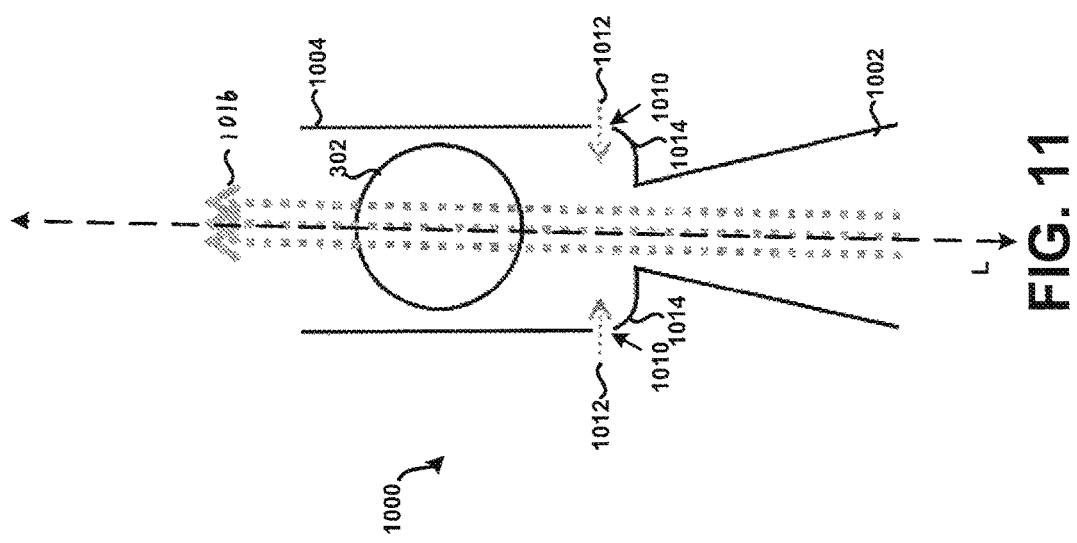
FIG. 11 shows a cross-section of a third example tubular body.

Further, it is contemplated that the tubular body 1000 may be fabricated to exhibit the arrangement or configuration of the apertures 1010 as shown in FIG. 10 together with the arrangement or configuration of the apertures 1010 as shown in FIG. 11. In either case, that is, in scenarios where the tubular body 1000 is fabricated to incorporated the apertures 1010 as shown in FIG. 10 or FIG. 11, or where the tubular body 1000 is fabricated to incorporate the apertures 1010 as shown in both FIG. 10 and FIG. 11, it is contemplated that the diameter of the apertures 1010 (i.e., when circular, however, other polygonal apertures are contemplated) in addition to the spatial arrangement of the apertures 1010 may be defined so that the desired fluid flow characteristics of the tubular body 1000 are realized. For example, the apertures 1010 may be defined within the tubular body 1000 so as to exhibit a specific pattern or symmetry that facilitates deposition of powder into the lungs of a patient, in tandem with preventing or at least minimizing the accumulation or build-up of powder in or near the corners 1014 of the tubular body 1000. Further, it is contemplated that the apertures 1010 may be formed or defined by means other than an injection molding technique for example.

Figure 12:
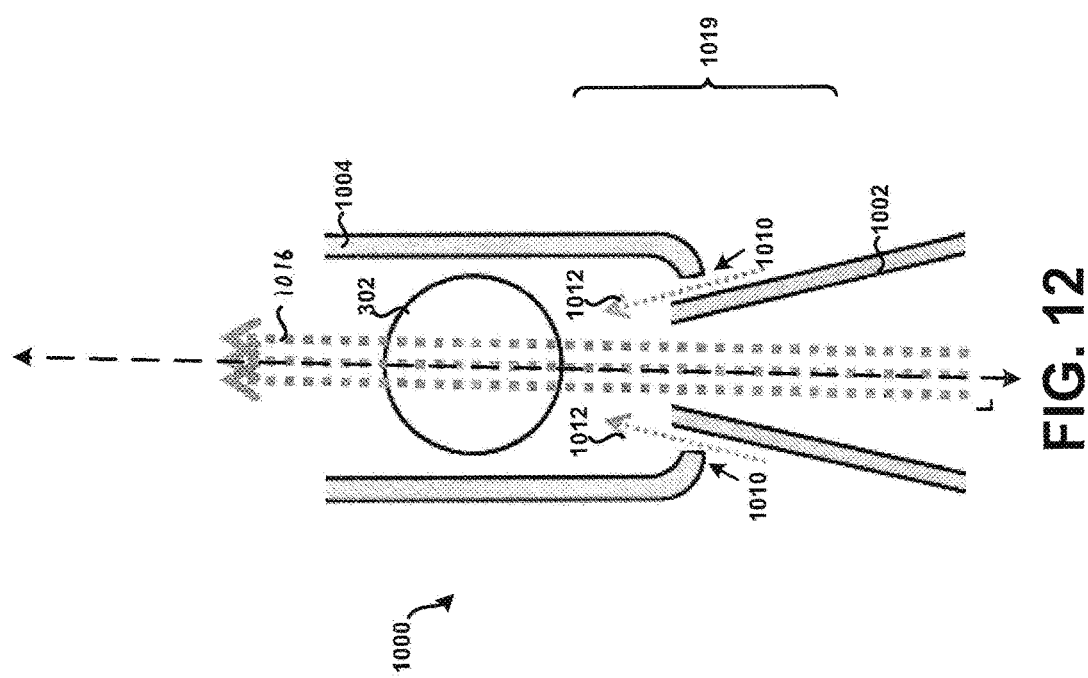
FIG. 12 shows a cross-section of a fourth example tubular body.

For example, referring now to FIG. 12, a cross-section of the second example tubular body 1000 is shown whereby the body of the inlet 1002 and the body of the dispersion chamber 1004 are not integral, but rather are separate pieces so that apertures 1010 are formed by a gap(s) between the body of the inlet 1002 and the body of the dispersion chamber 1004, when those two pieces are generally coupled together. In this example, the apertures 1010 are formed such that the secondary air flow 1012 comprises air flowing through the apertures 1010 and into the dispersion chamber 1004 in a substantially or approximately off-axis direction in reference to the primary air stream 1016 and/or the longitudinal axis L. It is contemplated that such a multi-piece arrangement or configuration may take many different forms, where a particular multi-piece arrangement or configuration may be implementation-specific, and/or possibly fabrication-method-specific, and so thus may evolve as requirements or specifications, and possibly fabrication technologies or techniques, evolve.

Figure 13:
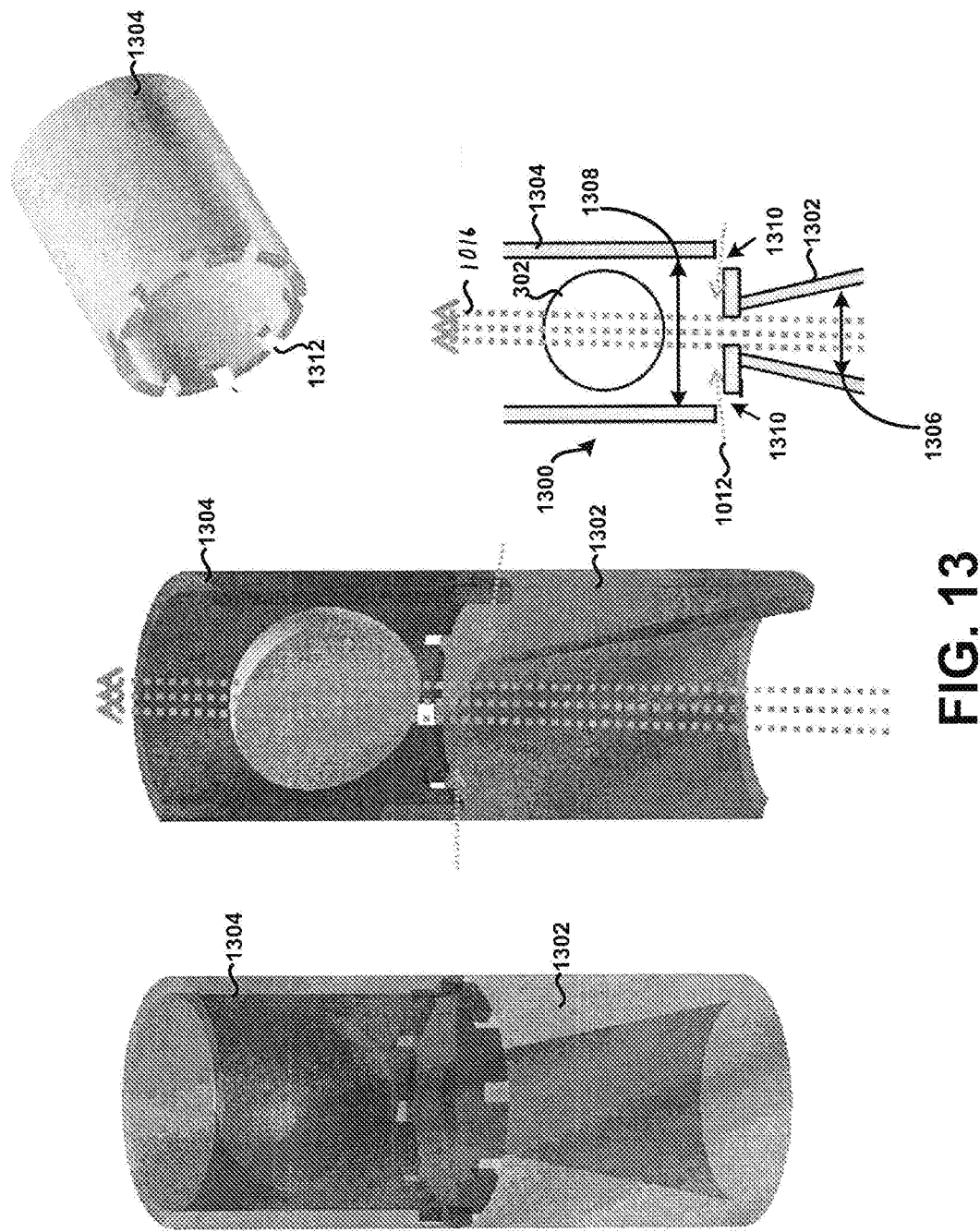
FIG. 13 shows a cross-section of a fifth example tubular body.

For example, referring now to FIG. 13, at least a cross-section of a third example tubular body 1300 having an inlet 1302 and a dispersion chamber 1304 is shown according to the principles of the present disclosure. In many aspects, the tubular body 1300 is similar to at least the tubular body 1000 of FIG. 10. For example, a fluid flow path of the inlet 1302 is defined by an internal diameter 1306 that varies or tapers along a longitudinal axis L, and a fluid flow path of the dispersion chamber 1304 is defined by an internal diameter 1308. Further, the body of the inlet 1302 and the body of the dispersion chamber 1304 are not integral, but rather are separate pieces so that one or more apertures 1310 are formed by a gap(s) between the body of the inlet 1302 and the body of the dispersion chamber 1304 when those two pieces are generally coupled together. More specifically, the dispersion chamber 1304 is formed to exhibit notches 1312, and when the body of the inlet 1302 and the body of the dispersion chamber 1304 are generally coupled, the apertures 1310 are formed as gaps between the body of the inlet 1302 and the body of the dispersion chamber 1304. In general, it is contemplated that the notches 1312 may be defined as desired so that the apertures 1310 exhibit a specific shape, pattern, and/or symmetry that facilitates deposition of powder into the lungs of a patient, in tandem with preventing or at least minimizing the accumulation or build-up of powder in or near internal surfaces of the mated assembly as shown in FIG. 13, and in particular the dispersion chamber 1304.

The features or aspects of the present disclosure may be beneficial and/or advantageous in many respects. For example, to help minimize the buildup or accumulation of powder within at least the above-described dispersion chambers, it is contemplated that the outside corners of the inlet surface of the chamber may be formed so that "small" amounts of air are allowed to flow into the outermost corner via a gap/holes at the outermost edge of the inlet surface and the chamber cylinder. The dimension of the gap or gaps may be critical so as to allow sufficient air to flow into the outermost corner to minimize or prevent powder buildup, essentially sweeping away or causing the powder trapped there by the eddies not to build up in the first place. The flow though still is low enough not to alter the linear oscillation characteristics of the bead, and the negative pressure field that is present in the chamber that draws the bead back toward the inlet when air flows into the main inlet to the chamber, and is above the level needed to make the bead oscillate. The "corner air flow" can be via holes in the corner, or via a designed-in gap caused by the design of the mating parts that make up the cylinder. It is contemplated that less than about 25% of the main flow, less than about 10% of the main, less than about 5% of the main flow, or less about than about 1% of the main flow may prevent powder buildup in the corners, depending on the characteristics of the powder deposited in the corners and the physical properties and components thereof.

Figure 21:
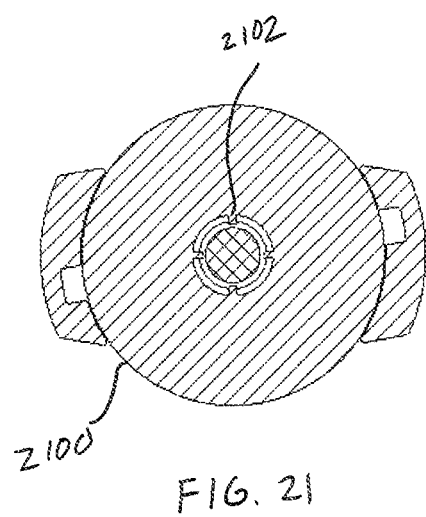
FIG. 21 shows one embodiment of chamber ribs.
Figure 22:
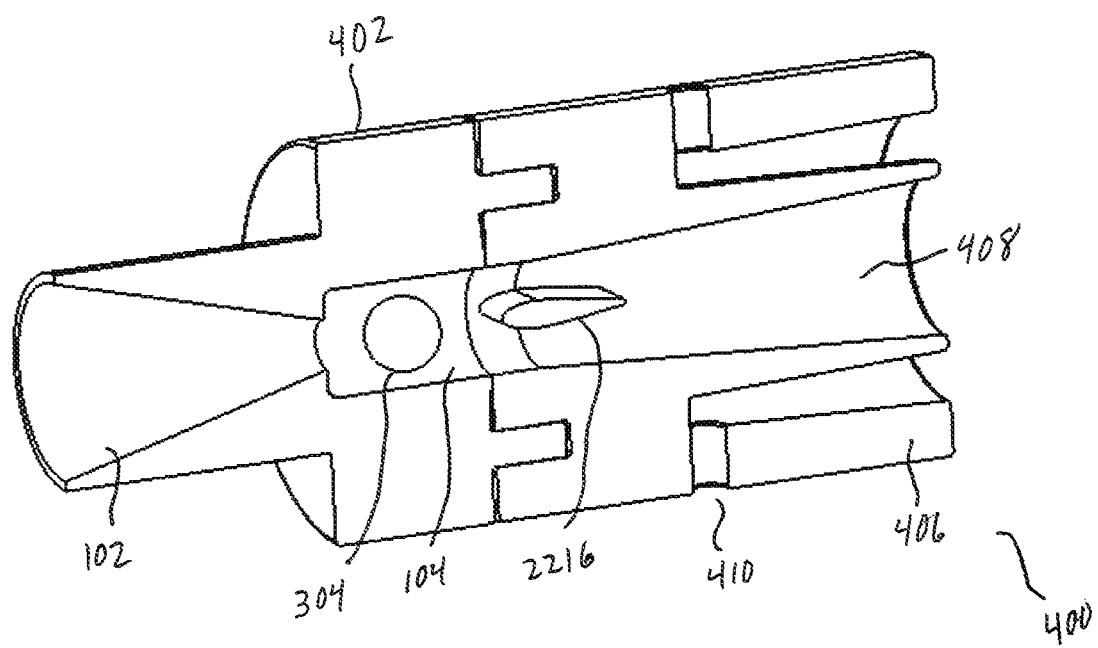
FIG. 22 shows one embodiments of bead retention features.
Figure 23:
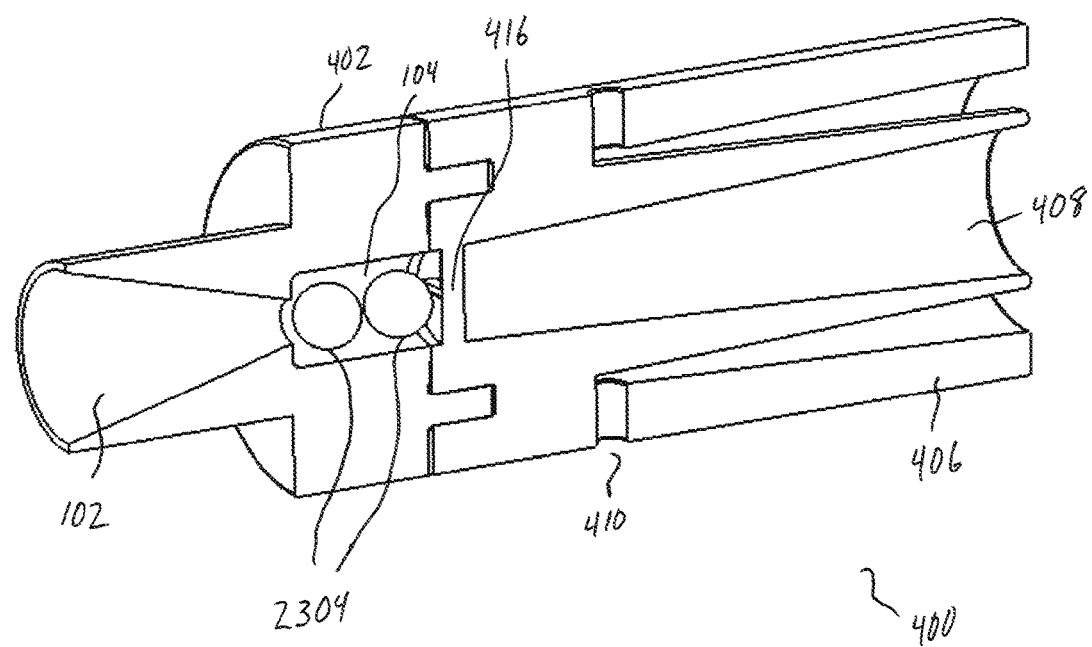
FIG. 23 shows an embodiment having two beads in a chamber.

Additional features could further improve the disruption and dispersion of powder agglomerates within the chamber by the bead. The additional features may include ribs 2102 in the chamber of inhaler 2100 as shown in FIG. 21 that would restrict the circumferential movement of the bead limiting the bead to axial movements. This may increase the speed and frequency of the bead oscillation in the chamber. In addition the retention feature 2216 that keeps the bead from exiting the chamber could be constructed from a wing as shown in cross section in FIG. 22. The wing as a retention feature 2216 could have several benefits to the design such as lowering inhaler resistance and increasing bead speed and or frequency among other possible benefits. In some embodiments, two or more beads 2304 may be placed in a single chamber as shown in FIG. 23, this may improve the disruption and dispersion of powder agglomerates within the chamber.

Figure 24:
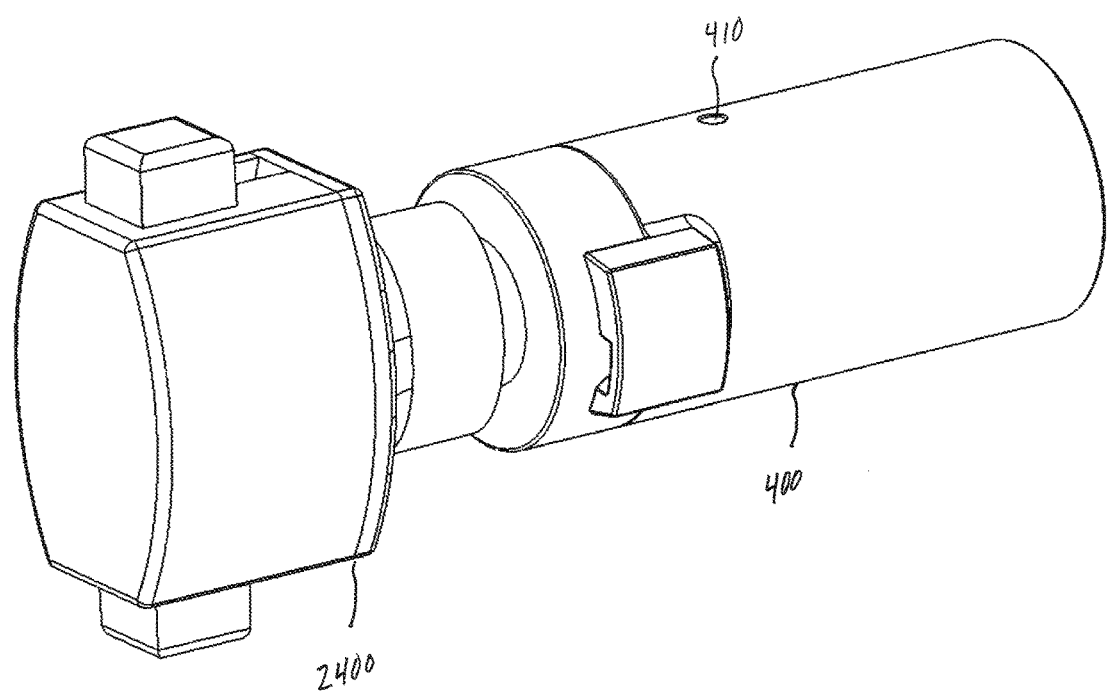
FIG. 24 shows an embodiment of a DPI with capsule piercing and powder feed element from a Plastiape RS01 inhaler.
Figure 26:
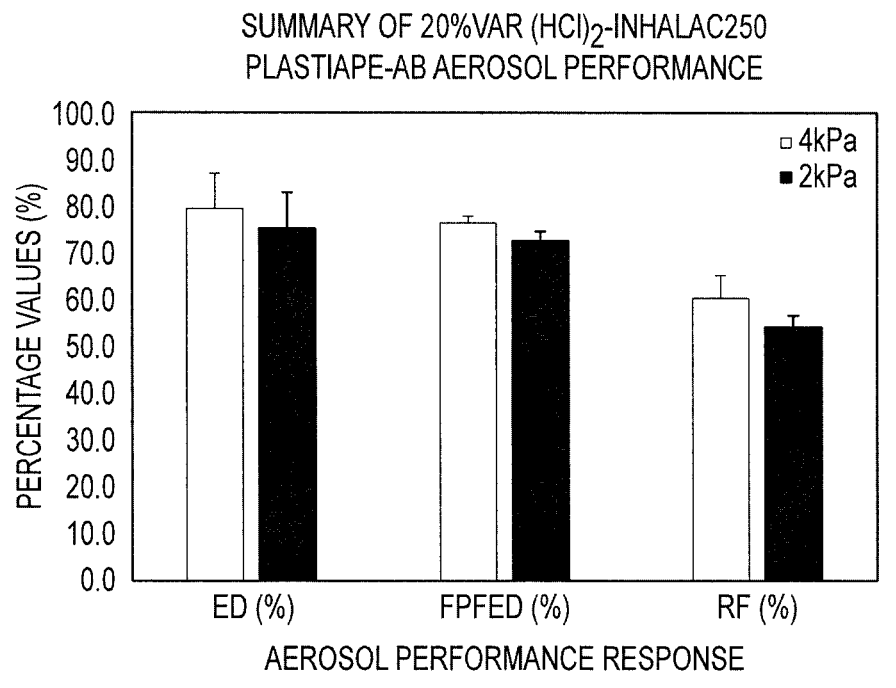

A specific embodiment of the inhaler 2400 has been created using the Plastiape RS01 dry powder inhaler (Plastiape S.p.a, Italy) as the dose containment and delivery system. This embodiment utilizes the capsule piercing and dose delivery system from a Plastiape RS01 to feed powder into the chamber with the oscillating actuator, a spherical bead as seen in FIGS. 24-25. After piercing a capsule 2402, air flows through inlet passages 2404 and the pierced capsule 2402 is lifted from the piercing chamber 2408 and rotates about its axis to efficiently empty the capsule 2402. The aerosolized powder exiting the rotating capsule 2402 flows through a grid that serves as a flow straightening element 2406 and is fed into the chamber with the oscillating spherical bead. The design utilizes a conical frustrum inlet from the Plastiape RS01 inhaler to the inlet diameter 106. Experiments using a Next Generation Impactor (NGI) with this design have shown an emitted fine particle fraction (% FPF, with a fine particle cutoff <5.3 μm) greater than 70% with several different active pharmaceutical ingredients (API). Emitted fine particle fraction (% FPF) is defined as the fraction of emitted mass below a cutoff diameter divided by the emitted mass from the inhaler. An experiment was performed testing this embodiment at 2 and 4 kPa with 20 mg 20% Vardenafil $(HCl)_2$ in a lactose blend. This inhaler 2400 used $d_{bead}$=4.00 mm, $d_{inlet}$=2.72 mm, $d_{chamber}$=5.89 mm, $l_{chamber}$=10 mm, with 2 bypass channels open which resulted in a resistance=0.104 (cm $H_2O^{0.5}$/LPM). Results show that this embodiment achieved similar aerosol performance at 2 and 4 kPa as shown in FIG. 26.

Figure 27:
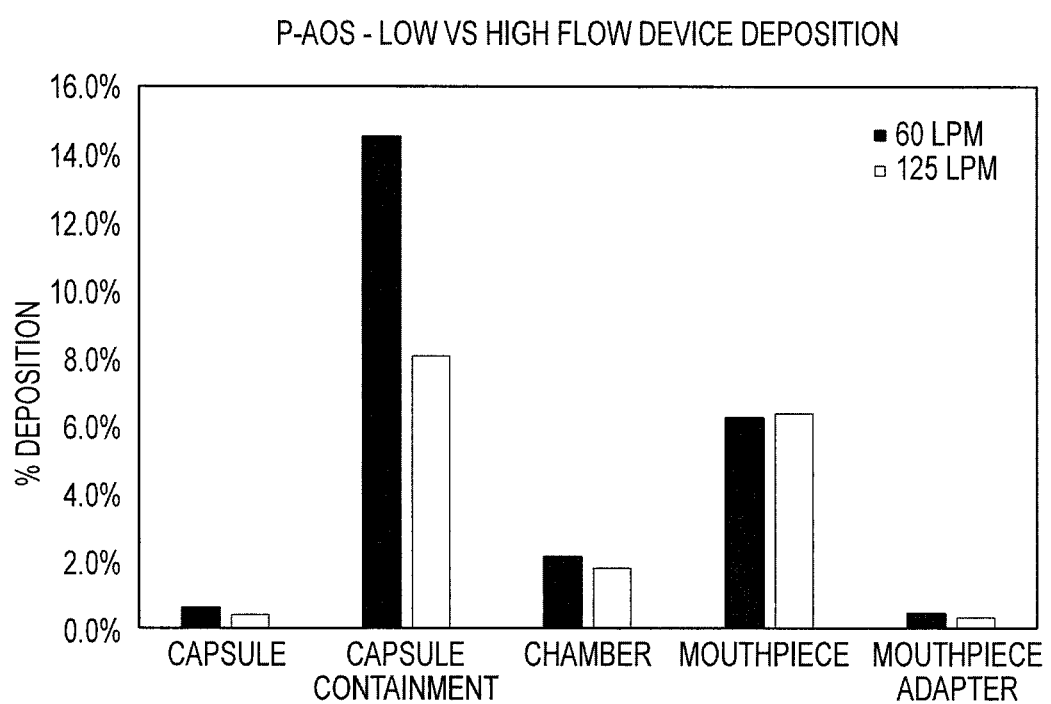
FIG. 27 shows drug deposition within the DPI of FIG. 24 at different flow rates.

Typically drug powder deposition on the inhaler device components in dry powder inhalers changes with air flow rate. An experiment was conducted using the embodiment exhibited in FIG. 24 and FIG. 25. This inhaler used $d_{bead}$=4.00 mm, $d_{inlet}$=2.72 mm, $d_{chamber}$=5.89 mm, $l_{chamber}$=10 mm, with 2 bypass channels which resulted in a resistance=0.104 (cm $H_2O^{0.5}$/LPM). The inhaler was loaded with 20 mg of 20% Vardenafil $(HCl)_2$ and the amount of drug deposited in the capsule containment 2400, dispersion chamber 104 and bead 304, and mouthpiece 406 components as shown in FIG. 27. The inhaler was tested at 60 and 150 LPM (4 and 24 kPa respectively). Surprisingly the drug deposition by % mass was largely unchanged in the dispersion chamber 104, bead 304, and mouthpiece 408 sections despite a 250% increase in inhaler flow as shown in TABLE 4.

TABLE 4

| Inhaler portion | 60 LPM | 150 LPM |
| --- | --- | --- |
| Capsule containment | 14.6% | 8.1% |
| Chamber and bead | 2.1% | 1.7% |
| Mouthpiece | 6.2% | 6.3% |

Although the subject matter has been described in language specific to structural features and/or methodological acts, it is to be understood that the subject matter defined in the appended claims is not necessarily limited to the specific features or acts described above. Rather, the specific features and acts described above are disclosed as example forms of implementing the claims.

What is claimed is:

1. A dry powder inhaler, comprising:
   a powder storage element configured to hold a powdered medicament;
   an inlet channel configured to receive powdered medicament from the powder storage element that is entrained in an airflow, the inlet channel having a portion with a first diameter and defining an opening;
   a dispersion chamber that is adapted to receive the airflow and the powdered medicament from the opening of the inlet channel, the dispersion chamber having a second diameter, wherein the dispersion chamber defines at least one aperture configured to receive chase air separate from the airflow entering in through the inlet channel;
   an actuator housed within the dispersion chamber, the actuator being configured to oscillate within the dispersion chamber when exposed to the airflow to deaggregate the powdered medicament entrained in the airflow passing through the dispersion chamber, wherein a ratio between the first diameter and the second diameter is between about 0.40 and 0.60 such that an audible sound is produced as the actuator oscillates; and
   an outlet channel through which the airflow and powdered medicament exit the inhaler for delivery to a patient.

2. The dry powder inhaler according to claim 1, wherein:
   the dispersion chamber has a length;
   the actuator has a diameter, and
   the length of the dispersion chamber is between about 2 and 3.5 times larger than the diameter of the actuator such that the audible sound is produced as the actuator oscillates.

3. The dry powder inhaler according to claim 1, wherein the opening is non-circular.

4. The dry powder inhaler according to claim 1, wherein the airflow is substantially coaxial with a longitudinal axis of the dispersion chamber.

5. The dry powder inhaler according to claim 1, wherein the powdered medicament is packaged in one or more blisters, one or more capsules, or one or more reservoirs.

6. The dry powder inhaler according to claim 1, wherein the inlet channel is conical frustrum shaped.

7. The dry powder inhaler according to claim 1, wherein the inlet channel comprises a flow straightener.

8. A dry powder inhaler, comprising:
a powder storage element configured to hold a powdered medicament;
an inlet channel configured to receive powdered medicament from the powder storage element that is entrained in an airflow, the inlet channel defining an opening;
a dispersion chamber that is adapted to receive the airflow and the powdered medicament from the opening of the inlet channel, the dispersion chamber having a length, wherein the dispersion chamber has a first end and a second end;
a bead housed within the dispersion chamber, the bead being configured to oscillate within the dispersion chamber when exposed to the airflow so as to deaggregate the powdered medicament entrained by the airflow passing through the dispersion chamber, the bead having a diameter, wherein:
the length of the dispersion chamber is between about 2 and 3.5 times larger than the diameter of the bead such that an audible sound is produced as the bead oscillates;
the bead rarely contacts the first end or the second end while oscillating due to the airflow; and
the airflow is caused by an inhalation of the patient; and
an outlet channel through which the airflow and powdered medicament exit the inhaler for delivery to a patient.

9. The dry powder inhaler according to claim 8, wherein the inlet channel is tapered from a first position to a smaller second position.

10. The dry powder inhaler according to claim 9, wherein the dispersion chamber defines at least one aperture configured to receive chase air separate from the airflow entering in through the inlet channel.

11. A dry powder inhaler, comprising:
a powder storage element configured to hold a powdered medicament, wherein the powdered medicament is contained within a capsule;
a piercing member configured to puncture the capsule;
an inlet channel configured to receive powdered medicament from the powder storage element that is entrained in an airflow, the inlet channel having a portion with a first diameter and defining an opening;
a dispersion chamber that is adapted to receive the airflow and the powdered medicament from the opening of the inlet channel, the dispersion chamber having a second diameter and a length;
a bead housed within the dispersion chamber, the bead being configured to oscillate within the dispersion chamber when exposed to the airflow to deaggregate the powdered medicament entrained by the airflow passing through the dispersion chamber, the bead having a third diameter, wherein a ratio between the first diameter and the second diameter is between about 0.40 and 0.66 and the length is between about 2 and 3.5 times larger than the third diameter such that an audible sound is produced as the bead oscillates; and
an outlet channel through which the airflow and powdered medicament exit the inhaler for delivery to a patient, wherein the powder storage element is configured to rotate the punctured capsule when exposed to the airflow to empty the powdered medicament from the punctured capsule.

12. The dry powder inhaler according to claim 11, wherein the inlet channel is conical frustrum shaped.

* * * * *